(12) United States Patent
Sakamoto et al.

(10) Patent No.: US 10,290,813 B2
(45) Date of Patent: *May 14, 2019

(54) MATERIAL FOR ORGANIC ELECTROLUMINESCENT DEVICE AND ORGANIC ELECTROLUMINESCENT DEVICE INCLUDING THE SAME

(71) Applicant: SAMSUNG DISPLAY CO., LTD., Yongin-si, Gyeonggi-do (KR)

(72) Inventors: Naoya Sakamoto, Yokohama (JP); Hiroaki Itoi, Yokohama (JP); Hiromi Nakano, Yokohama (JP); Hideo Miyake, Yokohama (JP); Ichinori Takada, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 132 days.

This patent is subject to a terminal disclaimer.

(21) Appl. No.: 14/919,627

(22) Filed: Oct. 21, 2015

(65) Prior Publication Data

US 2016/0118596 A1 Apr. 28, 2016

(30) Foreign Application Priority Data

Oct. 28, 2014 (JP) .................................. 2014-219468

(51) Int. Cl.
*H01L 51/00* (2006.01)
*H01L 51/50* (2006.01)
(Continued)

(52) U.S. Cl.
CPC ........ *H01L 51/0061* (2013.01); *C07C 211/54* (2013.01); *C07C 211/57* (2013.01);
(Continued)

(58) Field of Classification Search
None
See application file for complete search history.

(56) References Cited

U.S. PATENT DOCUMENTS 9,590,186 B2 * 3/2017 Itoi .................... H01L 51/0073
9,859,503 B2 * 1/2018 Hwang ............... H01L 51/0061
(Continued)

FOREIGN PATENT DOCUMENTS

EP 2 468 725 A1 6/2012
JP 2009-029726 A 2/2009
(Continued)

OTHER PUBLICATIONS

Machine-assisted English translation for JP2011-51936 (2011) provided by JPO.*

(Continued)

*Primary Examiner* — Sin J Lee
(74) *Attorney, Agent, or Firm* — Lewis Roca Rothgerber Christie LLP

(57) ABSTRACT

A material for an organic electroluminescent device having high emission efficiency and long life, and an organic electroluminescent device including the same. The material for an organic electroluminescent device may be represented by Formula (1).

Formula 1

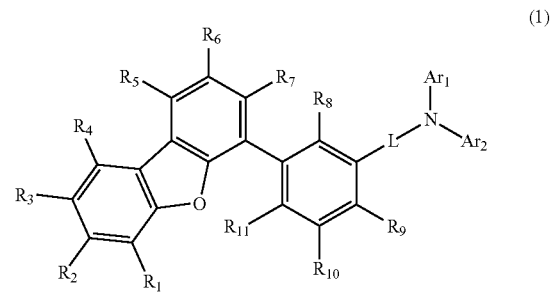

(1)

14 Claims, 2 Drawing Sheets

(51) Int. Cl.

| | | |
|---|---|---|
| *C09K 11/06* | (2006.01) | |
| *C09K 11/02* | (2006.01) | |
| *C07D 307/91* | (2006.01) | |
| *C07C 211/54* | (2006.01) | |
| *C07C 211/57* | (2006.01) | |
| *C07C 211/58* | (2006.01) | |
| *C07C 211/61* | (2006.01) | |

(52) U.S. Cl.
CPC .......... *C07C 211/58* (2013.01); *C07C 211/61* (2013.01); *C07D 307/91* (2013.01); *C09K 11/025* (2013.01); *C09K 11/06* (2013.01); *H01L 51/006* (2013.01); *H01L 51/0059* (2013.01); *H01L 51/0071* (2013.01); *H01L 51/0073* (2013.01); *H01L 51/5064* (2013.01); *H01L 51/0074* (2013.01); *H01L 51/5072* (2013.01)

(56) References Cited

U.S. PATENT DOCUMENTS

| | | | |
|---|---|---|---|
| 9,997,711 B2* | 6/2018 | Shin | ................... H01L 51/0054 |
| 2011/0278551 A1* | 11/2011 | Yabunouchi | ......... C07D 405/12 257/40 |
| 2012/0146014 A1 | 6/2012 | Kato | |
| 2012/0161119 A1 | 6/2012 | Yabunouchi | |
| 2016/0133848 A1* | 5/2016 | Balaganesan | ........ C07D 333/76 257/40 |
| 2016/0163994 A1* | 6/2016 | Park | ........................ C09K 11/06 257/40 |
| 2016/0204354 A1* | 7/2016 | Kang | ................... C07C 211/54 257/40 |
| 2017/0084843 A1* | 3/2017 | Yun | ..................... H01L 51/0061 |

FOREIGN PATENT DOCUMENTS

| | | |
|---|---|---|
| JP | 2009-267255 A | 11/2009 |
| JP | 2011-051936 A | 3/2011 |
| WO | WO 2009/145016 A1 | 12/2009 |
| WO | WO 2010/061824 A1 * | 6/2010 |
| WO | WO 2011/021520 A1 | 2/2011 |
| WO | WO2014104515 A1 * | 7/2014 |
| WO | WO2014196805 A1 * | 12/2014 |
| WO | WO 2015/041492 A1 * | 3/2015 |
| WO | WO2015034093 A1 * | 3/2015 |

OTHER PUBLICATIONS

English translation of WO 2014/104515A1 provided by WIPO. (Year: 2014).*
English translation of WO 2015/034093A1 provided by Google. (Year: 2015).*

* cited by examiner

MATERIAL FOR ORGANIC ELECTROLUMINESCENT DEVICE AND ORGANIC ELECTROLUMINESCENT DEVICE INCLUDING THE SAME

CROSS-REFERENCE TO RELATED APPLICATION

This patent application claims priority to and the benefit of Japanese Patent Application No. 2014-219468, filed on Oct. 28, 2014, the entire content of which is incorporated herein by reference.

BACKGROUND

The present disclosure herein relates to a material for an organic electroluminescent device and an organic electroluminescent device including the same, and more particularly, to a material for an organic electroluminescent device having high emission efficiency and long life (e.g., long lifespan) and an organic electroluminescent device including the same.

In recent years, organic electroluminescent (EL) displays as one kind of image displays have been actively developed. Unlike liquid crystal displays and the like, organic EL displays are so-called self-luminescent displays which display images by emitting light from a luminescent material including an organic compound in the emission layer through recombination of holes and electrons injected from an anode and a cathode in the emission layer.

An example of an organic EL device existing in the art is an organic EL device which includes an anode, a hole transport layer disposed on the anode, an emission layer disposed on the hole transport layer, an electron transport layer disposed on the emission layer, and a cathode disposed on the electron transport layer. Holes injected from the anode are injected via the hole transport layer into the emission layer. Meanwhile, electrons are injected from the cathode, and then injected via the electron transport layer into the emission layer. The holes and the electrons injected into the emission layer recombine to generate excitons within the emission layer. The organic EL device emits light generated by deactivation radiation of the excitons. Organic EL devices are not limited to the above-described configuration but may be changed to various suitable forms.

When organic EL devices are applied in display apparatuses, the high efficiency and long life (e.g., long lifespan) of the organic EL device are required. The driving voltage is high and the emission efficiency is insufficient in an organic EL device—particularly in a blue emission region when compared to a green emission region and a red emission region. To realize the high efficiency and long life of an organic EL device, ways of increasing the normalization, stabilization and durability of the hole transport layer have been examined.

As a hole transport material utilized in a hole transport layer, various compounds such as an aromatic amine compound have been utilized. However, issues related to resolving the short life (e.g., short lifespan) of the device remain. As a useful material for increasing the life (e.g., the lifespan) of the organic EL device, for example, an amine derivative substituted with an aryl group or a heteroaryl group has been suggested. However, an organic EL device utilizing the above-mentioned material has insufficient emission life. An aromatic amine compound having 4-dibenzofuran has been suggested as a charge transport material. However, the aromatic amine compound suggested has a high molecular weight, and defects concerning thermal stability may arise during the manufacture of an organic EL device. Thus, an organic EL device having higher efficiency, thermal stability and long emission life is required (or desired) at present. Particularly, since the emission efficiency of an organic EL device in a blue emission region is lower than in a red emission region and a green emission region, an increase in the emission efficiency in the blue emission region is required (or desired).

SUMMARY

Aspects of embodiments of the present disclosure provide for solving the above-mentioned tasks a material for an organic EL device having high emission efficiency and long life, and an organic EL device including the same.

Particularly, an aspect according to one or more embodiments of the present disclosure is directed towards a material for an organic EL device having high emission efficiency and long life in a blue emission region, and an organic EL device including the same in at least one layer of stacking layers (e.g., a plurality of layers stacked over one another) disposed between an emission layer and an anode.

According to an embodiment of the inventive concept, a material for an organic EL device is represented by Formula 1.

Formula 1

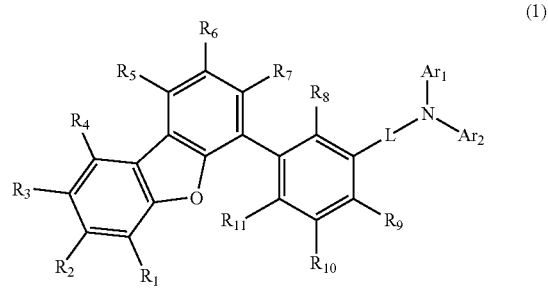

In Formula 1, $R_1$ to $R_{11}$ are each independently a substituted or unsubstituted aryl group having 6 to 30 carbon atoms for forming a ring, a substituted or unsubstituted heteroaryl group having 1 to 30 carbon atoms for forming a ring, an alkyl group having 1 to 15 carbon atoms, a substituted or unsubstituted silyl group, a halogen atom, hydrogen or deuterium; $Ar_1$ and $Ar_2$ are each independently an aryl group having 6 to 16 carbon atoms for forming a ring, or an alkyl group having 1 to 15 carbon atoms; and L is a direct linkage, a substituted or unsubstituted arylene group or a substituted or unsubstituted heteroarylene group.

The material for an organic EL device according to an embodiment introduces dibenzofuran at the meta position of a phenylene group combined with an amine group directly or via L. In the material for an organic EL device, polarization may be generated due to the oxygen atom of the dibenzofuran in a molecule because of the structural properties thereof, and the amorphous properties of the material may be improved (e.g., the crystallinity of the material may be decreased), thereby increasing the charge mobility and realizing long life and high emission efficiency. Particularly, remarkable effects may be obtained in a blue emission region.

In an embodiment, $Ar_1$ and $Ar_2$ may be each independently selected from the group consisting of a phenyl group, a biphenyl group, a naphthyl group, a phenylnaphthyl group and a naphthylphenyl group in the material for an organic EL device.

In the material for an organic EL device, $Ar_1$ and $Ar_2$ may be each independently the phenyl group, the biphenyl group, the naphthyl group, the phenylnaphthyl group, or the naphthylphenyl group, and thermal stability may be improved.

In an embodiment, L may be one of a direct linkage, a phenylene group or a biphenylene group in the material for an organic EL device, represented by Formula 1.

In the material for an organic EL device, L may be the direct linkage, the phenylene group or the biphenylene group, and thermal stability may be improved.

In an embodiment, $R_{10}$ may be hydrogen in the material for an organic EL device, represented by Formula 1.

In the material for an organic EL device, $R_{10}$ may be the hydrogen atom, and the amorphous properties thereof may be improved further, and long life and high emission efficiency may be realized.

In an embodiment of the inventive concept, an organic EL device includes an anode, an emission layer on the anode, and a plurality of stacking layers between the anode and the emission layer, and at least one of the plurality of stacking layers includes a material for an organic EL device represented by Formula 1.

Formula 1

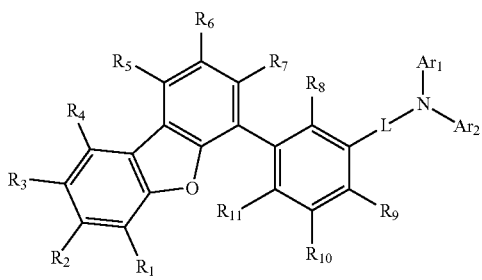

In Formula 1, $R_1$ to $R_{11}$ are each independently a substituted or unsubstituted aryl group having 6 to 30 carbon atoms for forming a ring, a substituted or unsubstituted heteroaryl group having 1 to 30 carbon atoms for forming a ring, an alkyl group having 1 to 15 carbon atoms, a substituted or unsubstituted silyl group, a halogen atom, hydrogen or deuterium; $Ar_1$ and $Ar_2$ are each independently an aryl group having 6 to 16 carbon atoms for forming a ring, or an alkyl group having 1 to 15 carbon atoms; and L is a direct linkage, a substituted or unsubstituted arylene group or a substituted or unsubstituted heteroarylene group.

In an embodiment, the plurality of stacking layers may include a hole transport layer, and the hole transport layer may include the material represented by Formula 1.

The organic EL device according to an embodiment utilizes the material for an organic EL device in a layer of stacking layers between an emission layer and an anode, and the long life and high emission efficiency thereof may be realized. Particularly, remarkable effects may be obtained in a blue emission region.

In an embodiment of the inventive concept, an organic EL device includes an anode, an emission layer on the anode, and a plurality of stacking layers between the anode and the emission layer, and the emission layer includes a material for an organic EL device represented by Formula 1 as a host material.

Formula 1

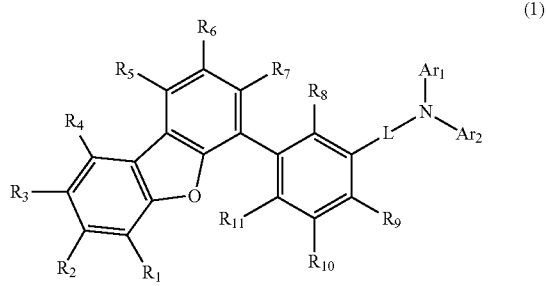

In Formula 1, $R_1$ to $R_{11}$ are each independently a substituted or unsubstituted aryl group having 6 to 30 carbon atoms for forming a ring, a substituted or unsubstituted heteroaryl group having 1 to 30 carbon atoms for forming a ring, an alkyl group having 1 to 15 carbon atoms, a substituted or unsubstituted silyl group, a halogen atom, hydrogen or deuterium; $Ar_1$ and $Ar_2$ are each independently an aryl group having 6 to 16 carbon atoms for forming a ring, or an alkyl group having 1 to 15 carbon atoms; and L is a direct linkage, a substituted or unsubstituted arylene group or a substituted or unsubstituted heteroarylene group.

The organic EL device according to an embodiment utilizes one of the materials for an organic EL device represented by Formula 1 as a host material, and the long life and high emission efficiency thereof may be realized. Particularly, remarkable effects may be obtained in a blue emission region.

BRIEF DESCRIPTION OF THE FIGURES

The accompanying drawings are included to provide a further understanding of the inventive concept, and are incorporated in and constitute a part of this specification. The drawings illustrate example embodiments of the inventive concept and, together with the description, serve to explain principles of the inventive concept. In the drawings.

DETAILED DESCRIPTION

Figure 1:
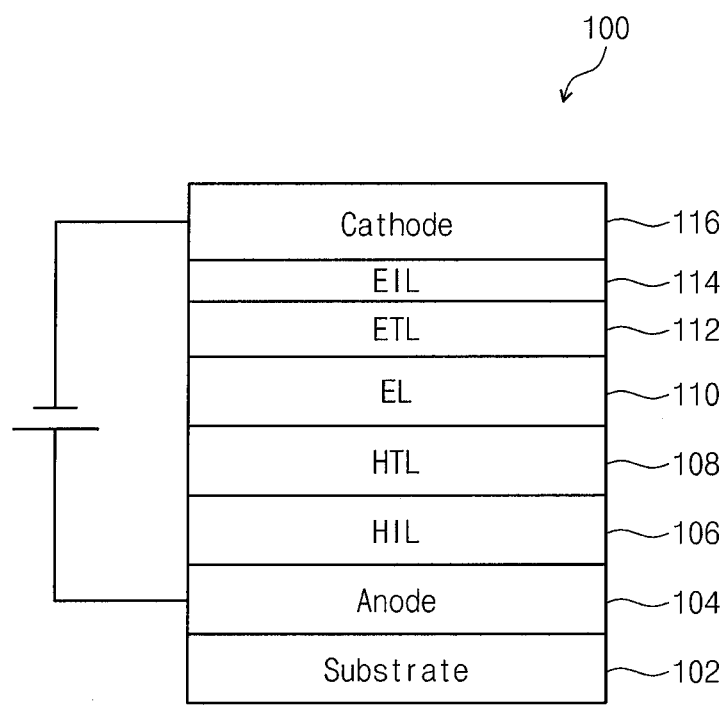
FIG. 1 is a schematic diagram of an organic EL device 100 according to an embodiment of the inventive concept.

To solve the above-described tasks, dibenzofuran is introduced at the meta position of a phenylene group combining with (e.g., linked to) a nitrogen atom (N) of an amine group directly or via a linker (L) in a material for an organic EL device according to an embodiment. Thus, the amorphous properties of the material may be improved, charge mobility may be increased, and long life and high emission efficiency may be realized.

Hereinafter, a material for an organic EL device and an organic EL device including the same according to the inventive concept will be described in more detail with reference to the accompanying drawings. The material for an organic EL device and the organic EL device including the same according to the inventive concept may, however, be embodied in different forms and should not be construed as limited to the embodiments set forth herein. In the description and drawings, elements having substantially the same function are designated by the same reference numerals, and repeated explanation thereof will be omitted.

The material for an organic EL device according to an embodiment may be an amine compound represented by the following Formula 1, in which dibenzofuran is introduced at the meta position of a phenylene group combined with (e.g., linked to) an amine group.

Formula 1

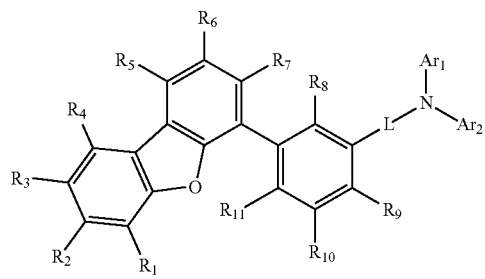

According to an embodiment, in the material for an organic EL device represented by Formula 1, $R_1$ to $R_{11}$ are each independently a substituted or unsubstituted aryl group having 6 to 30 carbon atoms for forming a ring, a substituted or unsubstituted heteroaryl group having 1 to 30 carbon atoms for forming a ring, an alkyl group having 1 to 15 carbon atoms, a substituted or unsubstituted silyl group, a halogen atom, hydrogen or deuterium. $Ar_1$ and $Ar_2$ are each independently an aryl group having 6 to 16 carbon atoms for forming a ring, or an alkyl group having 1 to 15 carbon atoms. L is a direct linkage, a substituted or unsubstituted arylene group or a substituted or unsubstituted heteroarylene group.

Herein, the substituted or unsubstituted aryl group having 6 to 30 carbon atoms for forming a ring utilized in $R_1$ to $R_{11}$ in Formula 1 may include, for example, a phenyl group, a naphthyl group, an anthracenyl group, a phenanthryl group, a biphenyl group, a terphenyl group, a quaterphenyl group, a quinquephenyl group, a fluorenyl group, a triphenylene group, a biphenylene group, a pyrenyl group, a benzofluoranthenyl group, a glyceryl group, etc., however, the substituted or unsubstituted aryl group having 6 to 30 carbon atoms for forming a ring utilized in $R_1$ to $R_{11}$ in Formula 1 is not limited thereto.

The substituted or unsubstituted heteroaryl group having 1 to 30 carbon atoms for forming a ring utilized in $R_1$ to $R_{11}$ may include, for example, a pyridyl group, a furyl group, a thienyl group, a quinolyl group, an isoquinolyl group, a benzofuryl group, a benzothienyl group, an indolyl group, a benzoxazolyl group, a benzothiazolyl group, a quinoxalyl group, a benzoimidazolyl group, a dibenzofuryl group, a dibenzothienyl group, a carbazolyl group, etc., however, the substituted or unsubstituted heteroaryl group having 1 to 30 carbon atoms for forming a ring utilized in $R_1$ to $R_{11}$ is not limited thereto.

The alkyl group having 1 to 15 carbon atoms utilized as $R_1$ to $R_{11}$ may include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibrimoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, a cyclopropyl group, a cyclobutyl group, a cyclopentyl group, a cyclohexyl group, a 4-methylcyclohexyl group, a 1-adamantyl group, a 2-adamantyl group, a 1-norbornyl group, a 2-norbornyl group, etc., however, the alkyl group having 1 to 15 carbon atoms utilized as $R_1$ to $R_{11}$ is not limited thereto.

In addition, the silyl group utilized as $R_1$ to $R_{11}$ may include a trialkylsilyl group, a triarylsilyl group, a monoalkyldiarylsilyl group and/or a dialkylmonoarylsilyl group, and may be, for example, a trimethylsilyl group, a triphenylsilyl group, etc.

The halogen atom utilized as $R_1$ to $R_{11}$ may include a fluorine atom (F), a chlorine atom (Cl) and/or a bromine atom (Br).

In addition, $R_1$ to $R_{11}$ may be hydrogen or deuterium. In one embodiment, in Formula 1, $R_{10}$ may be hydrogen. In the case that $R_{10}$ is the hydrogen atom, the symmetry of the whole molecule represented by Formula 1 may be deteriorated, and the amorphous properties of the material may be improved.

In Formula 1, a plurality of adjacent $R_1$ to $R_{11}$ may combine with each other and may form a saturated or unsaturated ring.

In Formula 1, the aryl group having 6 to 16 carbon atoms for forming a ring utilized as $Ar_1$ and $Ar_2$ may include a phenyl group, a naphthyl group, an anthracenyl group, a phenanthryl group, a biphenyl group, a phenylnaphthyl group, a naphthylphenyl group, etc., without being limited thereto. In one embodiment, $Ar_1$ and $Ar_2$ may be each independently a phenyl group, a biphenyl group, a naphthyl group, a phenylnaphthyl group or a naphthylphenyl group.

The alkyl group having 1 to 15 carbon atoms utilized as $Ar_1$ to $Ar_2$ may include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibrimoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, a cyclopropyl group, a cyclobutyl group, a cyclopentyl group, a cyclohexyl group, a 4-methylcyclohexyl group, a 1-adamantyl group, a 2-adamantyl group, a 1-norbornyl group, a 2-norbornyl group, etc., however, the alkyl group having 1 to 15 carbon atoms utilized as $Ar_1$ to $Ar_2$ is not limited thereto.

L in Formula 1 is a direct linkage or a substituted or unsubstituted arylene group or heteroarylene group, and may be, for example, a phenylene group, a biphenylene group, a naphthylene group, an anthracenyl group, a fluorenylene group, a triphenylene group, a pyridylene group, a dibenzofurylene group, a dibenzoethynylene group, etc., without being limited thereto. In one embodiment, L may be a phenylene group or a biphenylene group.

As described above, the material for an organic EL device according to an embodiment is an amine compound in which dibenzofuran is introduced at (e.g., is linked at) the meta position of a phenylene group combined with (e.g., linked to) an amine group, and the phenylene group and the dibenzofuran are linked to each other at the 4th carbon of the dibenzofuran and the meta position of the phenylene group with respect to the position where the amine group is linked to the phenylene group. By introducing the dibenzofuran at the meta position of the phenylene group, where the effect of the substituent of the phenylene group is small, combined with the amine group directly or via a linker (L), polarization may be generated in a molecule due to the oxygen atom of the dibenzofuran, and the amorphous properties of the material may be increased and charge mobility may be increased. Thus, improved lifespan may be maintained, and high emission efficiency may be realized.

In the material for an organic EL device according to an embodiment, $Ar_1$ and $Ar_2$ in Formula 1 may be one of a phenyl group, a biphenyl group, a naphthyl group, a phenylnaphthyl group and a naphthylphenyl group. In one embodiment, L may be a phenylene group or a biphenylene group.

If the molecular weight of the material for an organic EL device is too large, the material is not applicable in an evaporation process. Thus, the desirable molecular weight of the material for an organic EL device may be equal to or less than about 1,000, and in one embodiment, may be equal to or less than about 800.

The material for an organic EL device according to an embodiment may be one of the compounds 1 to 6 below.

1

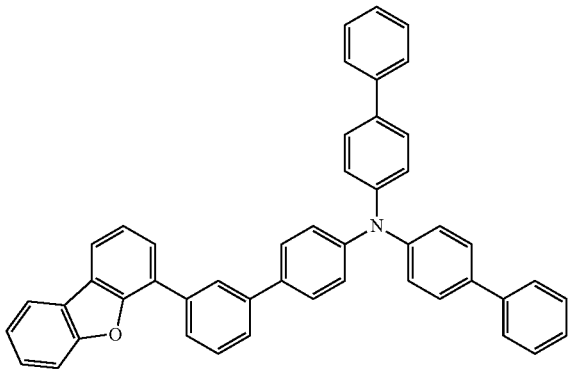

2

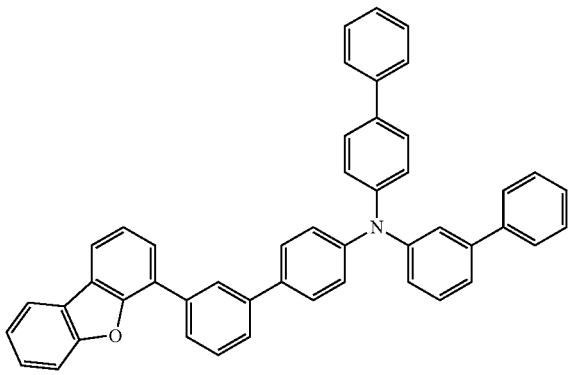

3

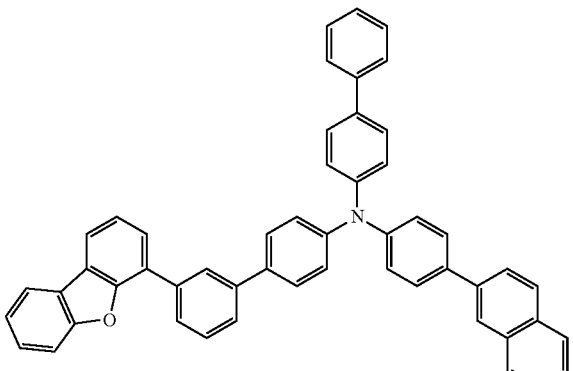

4

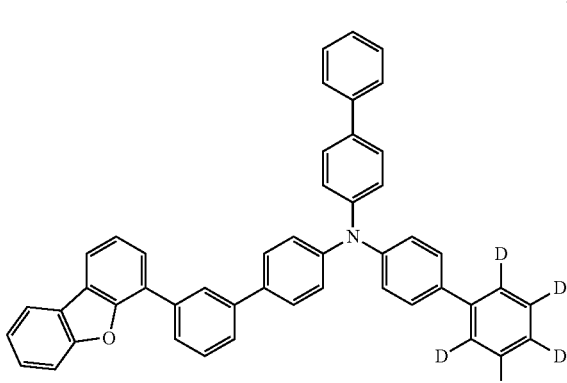

5
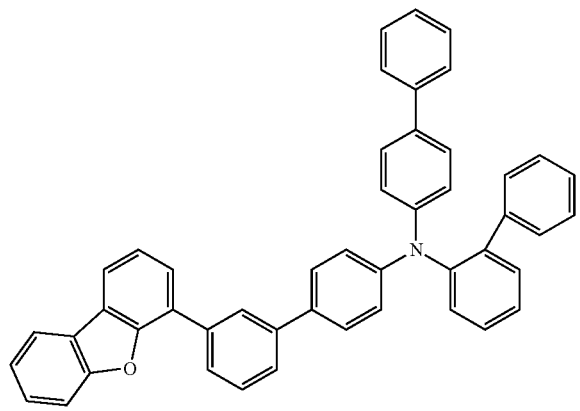
6
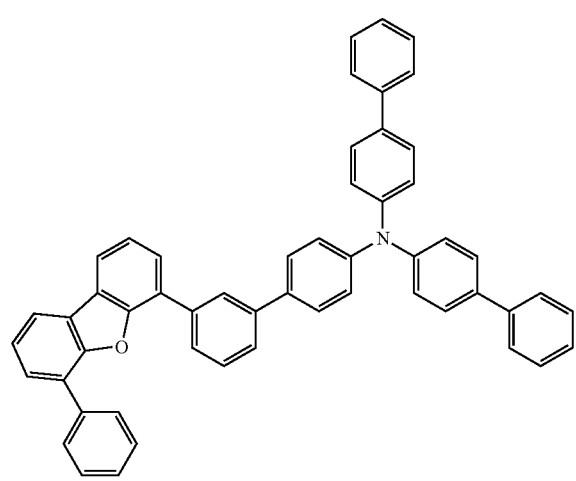
The material for an organic EL device according to an embodiment may be one of the compounds 7 to 12 below.
7
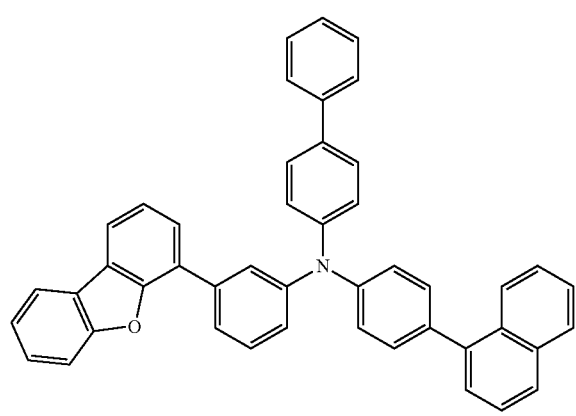
8
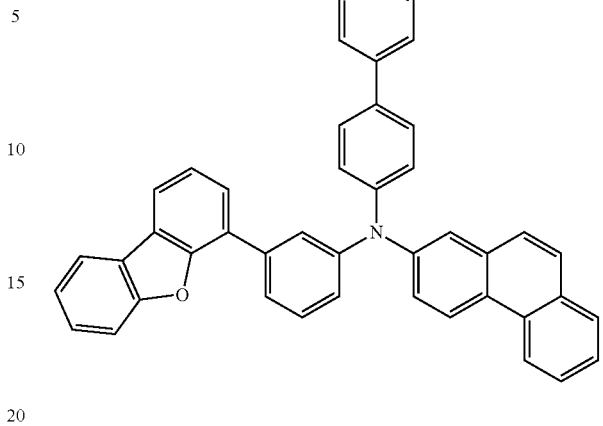
9
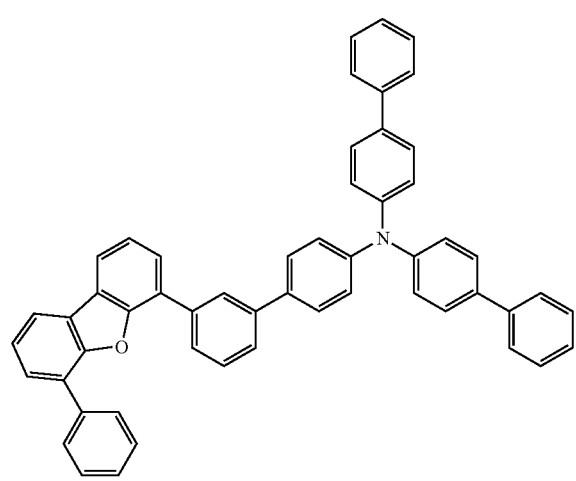
10
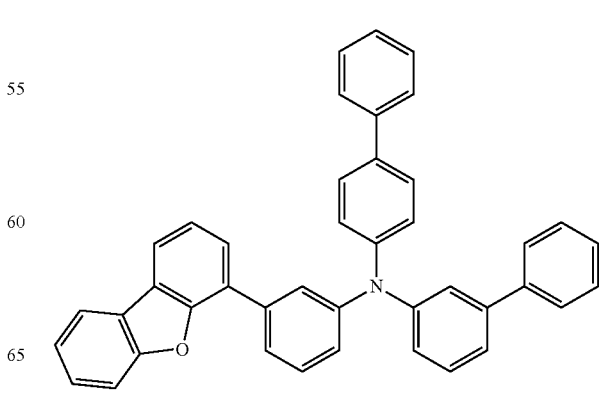

11
-continued
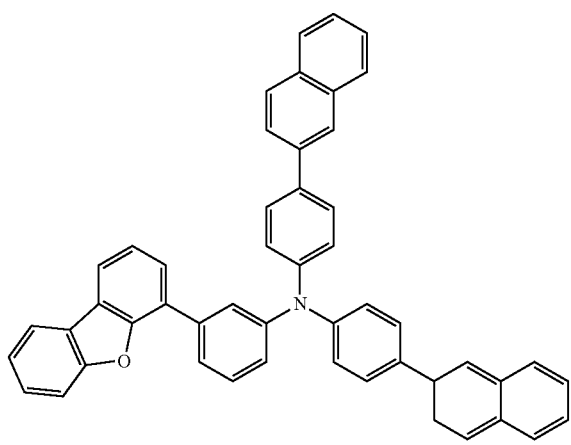
12
-continued
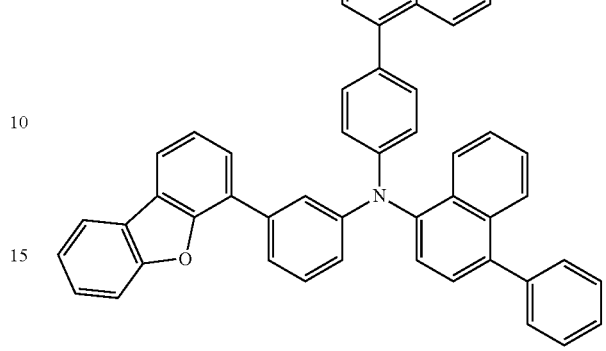
The material for an organic EL device according to an embodiment may be one of the compounds 13 to 19 below.
13
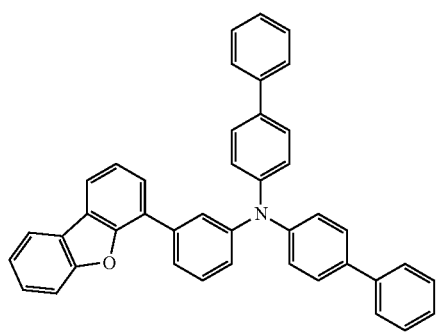
14
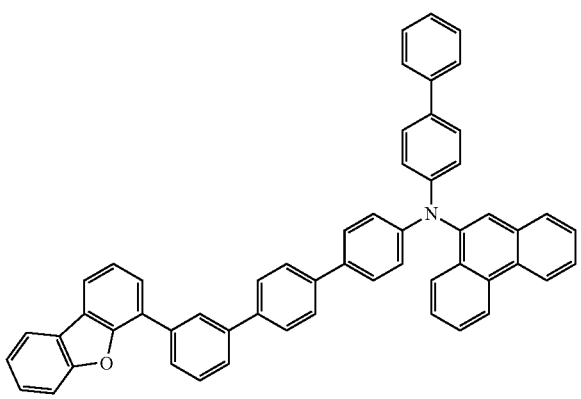
15
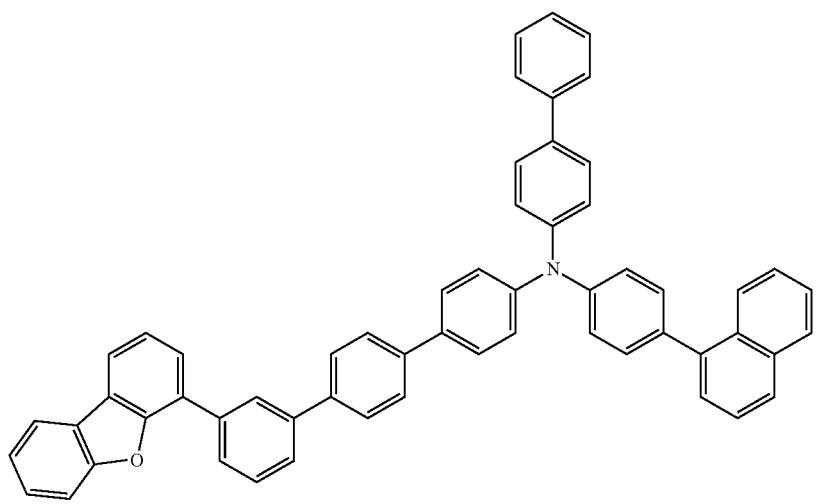

16
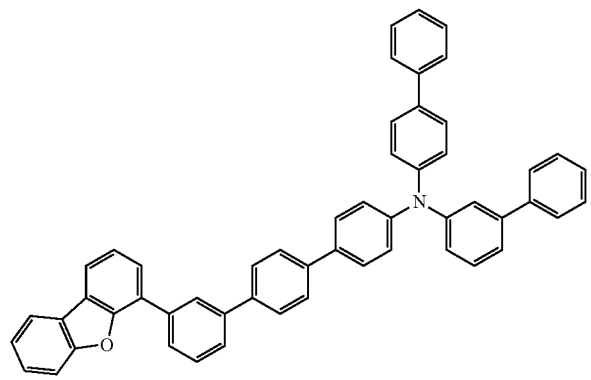
17
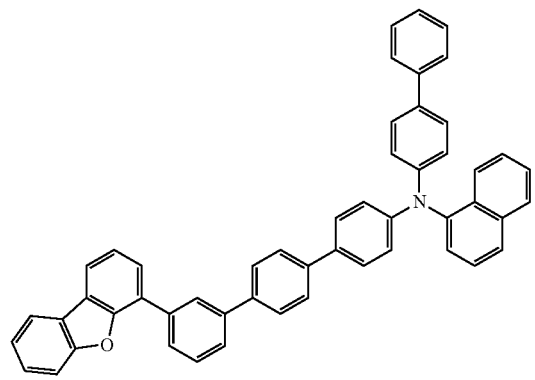
18
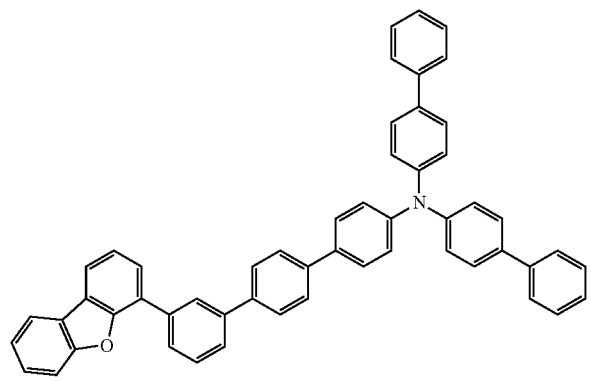
19
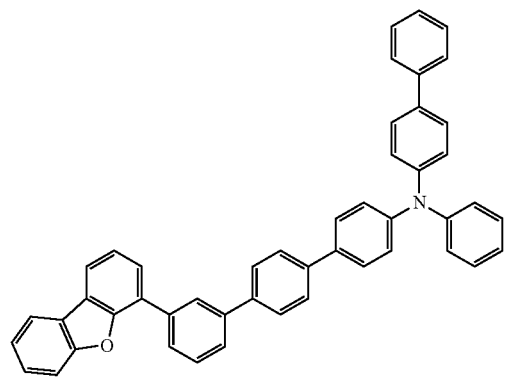
The material for an organic EL device according to an embodiment may be one of the compounds 20 to 22 below.
20
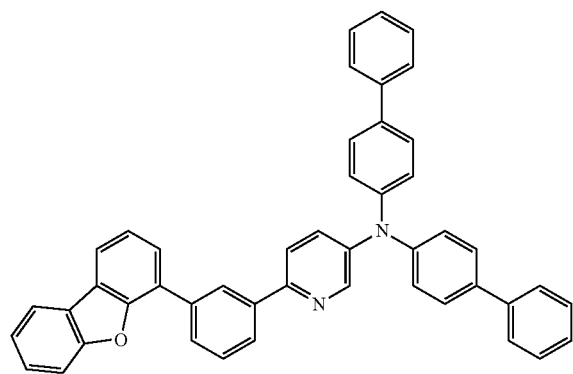

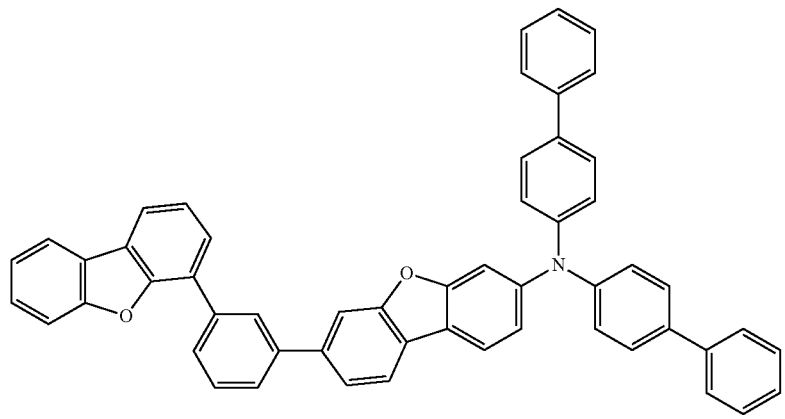

21

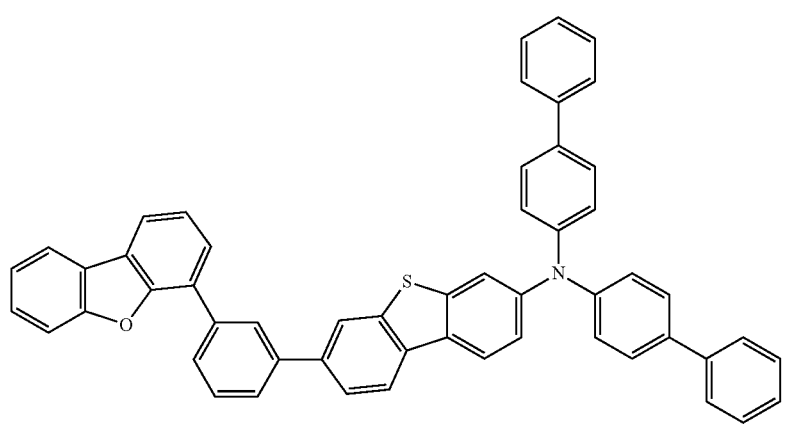

22

The material for an organic EL device according to an embodiment may be included in at least one layer of stacking layers (e.g., one layer of a plurality of layers stacked over one another) disposed between an emission layer and an anode. Thus, the amorphous properties of the material may be improved, charge mobility may be increased, and the long life and high efficiency of the organic EL device may be realized.

In addition, the material for an organic EL device according to an embodiment may be utilized as the host material of the emission layer of the organic EL device. The long life and high efficiency of the organic EL device may be also realized by utilizing the material for an organic EL device represented by Formula 1 as the host material of the emission layer.

(Organic EL Device)

An organic EL device including the material for an organic EL device according to another embodiment of the inventive concept will be explained.

The organic EL device may include an anode, an emission layer and a plurality of stacking layers disposed between the anode and the emission layer, and may include a material for an organic EL device represented by the following Formula 1 in at least one layer of the plurality of stacking layers.

Formula 1

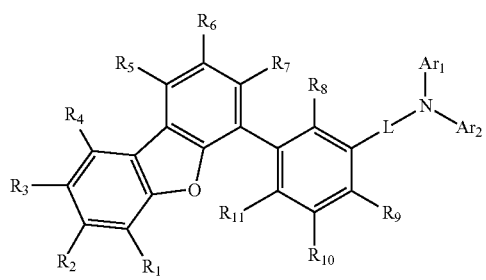

(1)

In Formula 1, $R_1$ to $R_{11}$ are each independently a substituted or unsubstituted aryl group having 6 to 30 carbon atoms for forming a ring, a substituted or unsubstituted heteroaryl group having 1 to 30 carbon atoms for forming a ring, an alkyl group having 1 to 15 carbon atoms, a substituted or unsubstituted silyl group, a halogen atom, hydrogen or deuterium. $Ar_1$ and $Ar_2$ are each independently an aryl group having 6 to 16 carbon atoms for forming a ring, or an alkyl group having 1 to 15 carbon atoms. L is a direct linkage, a substituted or unsubstituted arylene group, or a substituted or unsubstituted heteroarylene group.

FIG. 1 is a schematic diagram illustrating an organic EL device 100 according to an embodiment of the inventive concept. The organic EL device 100 may include, for example, a substrate 102, an anode 104, a hole injection layer 106, a hole transport layer 108, an emission layer 110, an electron transport layer 112, an electron injection layer 114 and a cathode 116. In an embodiment, the material for an organic EL device according to an embodiment of the inventive concept may be utilized in at least one layer of a plurality of stacking layers disposed between the emission layer and the anode.

In addition, in the organic EL device according to an embodiment, the material for an organic EL device represented by Formula 1 may be utilized as the host material of the emission layer.

Hereinafter, an embodiment utilizing the material for an organic EL device according to the inventive concept in the hole transport layer 108 will be explained.

The substrate 102 may be a transparent glass substrate, a semiconductor substrate formed utilizing silicon, or a flexible substrate formed of a resin, etc.

The anode 104 may be disposed on the substrate 102 and may be formed utilizing indium tin oxide (ITO), indium zinc oxide (IZO), etc.

The hole injection layer (HIL) 106 may be formed on the anode 104 and may be formed utilizing an existing material to a thickness within a range from about 10 nm to about 150 nm. Examples of a hole injection material may include triphenylamine-containing polyether ketone (TPAPEK), 4-isopropyl-4'-methyldiphenyliodoniumtetrakis(pentafluorophenyl)borate (PPBI), N,N'-diphenyl-N,N'-bis-[4-(phenyl-m-tolyl-amino)-phenyl]-phenyl-4,4'-diamine (DNTPD), a phthalocyanine compound such as copper phthalocyanine, 4,4',4''-tris(3-methyl phenyl phenylamino)triphenylamine (m-MTDATA), N,N'-di(1-naphthyl)-N,N'-diphenylbenzidine (NPB), 4,4',4''-tris{N,N-diphenyl amino}triphenylamine (TDATA), 4,4',4''-tris(N,N-2-naphthyl phenylamino)triphenylamine (2-TNATA), polyaniline/dodecylbenzenesulfonic acid (PANI/DBSA), poly(3,4-ethylenedioxythiophene)/poly(4-styrenesulfonate) (PEDOT/PSS), polyaniline/camphorsulfonic acid (PANI/CSA), polyaniline/poly(4-styrenesulfonate) (PANI/PSS), etc.

The hole transport layer (HTL) 108 may be formed on the hole injection layer 106 to a thickness within a range from about 10 nm to about 150 nm utilizing the material for an organic EL device represented by Formula 1 according to the inventive concept. The hole transport layer 108 including the material for an organic EL device represented by Formula 1 according to an embodiment may be formed by vacuum evaporation.

In the case that the material for an organic EL device represented by Formula 1 according to an embodiment is utilized as the host material of the emission layer (EL) 110, the hole transport layer 108 may be formed utilizing an existing hole transport material.

As the existing hole transport material, for example, 1,1-bis[(di-4-tolylamino)phenyl]cyclohexane (TAPC), a carbazole derivative such as N-phenylcarbazole and polyvinyl carbazole, N,N'-bis(3-methylphenyl)-N,N'-diphenyl-[1,1-biphenyl]-4,4'-diamine (TPD), 4,4',4''-tris(N-carbazolyl)triphenylamine (TCTA), N,N'-di(1-naphthyl)-N,N'-diphenylbenzidine (NPB), etc. may be utilized.

The emission layer (EL) 110 may be formed on the hole transport layer 108 utilizing an existing host material to a thickness within a range from about 10 nm to about 60 nm. As the existing host material utilized in the emission layer 110, for example, tris(8-quinolinolato)aluminum (Alq3), 4,4'-N,N'-dicarbazole-biphenyl (CBP), poly(n-vinylcarbazole) (PVK), 9,10-di(naphthalene-2-yl)anthracene (ADN), 4,4',4''-tris(N-carbazolyl)triphenylamine (TCTA), 1,3,5-tris (N-phenylbenzimidazole-2-yl)benzene (TPBI), 3-tert-butyl-9,10-di(naphtho-2-yl)anthracene (TBADN), distyrylarylene (DSA), 4,4'-bis(9-carbazole)-2,2'-dimethyl-biphenyl (dm-CBP), etc., may be utilized.

The emission layer may further include a dopant and the dopant material of the emission layer 110 may include a styryl derivative (for example, 1,4-bis[2-(3-N-ethylcarbazolyl)vinyl]benzene (BCzVB), 4-(di-p-tolylamino)-4'-[(di-p-tolylamino)styryl]stilbene (DPAVB), or N-(4-((E)-2-(6-((E)-4-(diphenylamino)styryl)naphthalene-2-yl)vinyl) phenyl-N-phenylbenzenamine (N-BDAVBi)), perylene and the derivative thereof (for example, 2,5,8,11-tetra-t-butylperylene (TBPe)), pyrene and the derivative thereof (for example, 1,1-dipyrene, 1,4-dipyrenylbenzene, or 1,4-bis(N, N-diphenylamino)pyrene), etc., without being limited thereto.

The electron transport layer (ETL) 112 may be formed on the emission layer 110 to a thickness within a range from about 15 nm to about 50 nm utilizing, for example, Alq3 or a material having a nitrogen-containing aromatic ring (for example, a material including a pyridine ring such as 1,3, 5-tri[(3-pyridyl)-phen-3-yl]benzene, a material including a triazine ring such as 2,4,6-tris(3'-(pyridine-3-yl)biphenyl-3-yl)1,3,5-triazine, or a material including an imidazole derivative such as 2-(4-N-phenylbenzoimidazolyl-1-ylphenyl)-9,10-dinaphthylanthracne).

The electron injection layer (EIL) 114 may be formed on the electron transport layer 112 to a thickness within a range from about 0.3 nm to about 9 nm utilizing, for example, a material including lithium fluoride (LiF), lithium-8-quinolinolato (Liq), etc.

The cathode 116 may be disposed on the electron injection layer 114 and may be formed utilizing a metal such as aluminum (Al), silver (Ag), lithium (Li), magnesium (Mg), calcium (Ca), etc., a mixture thereof, or a transparent material such as ITO or IZO.

Each electrode and each layer forming the organic EL device according to an embodiment may be formed by selecting an appropriate layer forming method in consideration of the materials utilized, for example, a vacuum evaporation method, a sputtering method, various coating methods, etc. As described above, the hole transport layer 108 formed utilizing the material for an organic EL device represented by Formula 1 according to an embodiment may be formed by vacuum evaporation.

In the organic EL device 100 according to an embodiment, a hole transport layer realizing the long life and high efficiency of the organic EL device may be formed utilizing the material for an organic EL device represented by Formula 1 according to an embodiment.

In the organic EL device 100 according to an embodiment, the material for an organic EL device according to an embodiment may be utilized as the material of a hole injection layer or the host material of an emission layer. As described above, the high efficiency and long life of the organic EL device may be realized by including the material for an organic EL device represented by Formula 1 according to an embodiment in at least one layer of a plurality of organic layers disposed between the emission layer and the anode.

In addition, the material for an organic EL device according to an embodiment may be applied in an organic EL device of an active matrix type utilizing a thin film transistor (TFT).

(Preparation Method)
The material for an organic EL device according to an embodiment may be synthesized, for example, as follows.
Synthetic Method of Compound 1
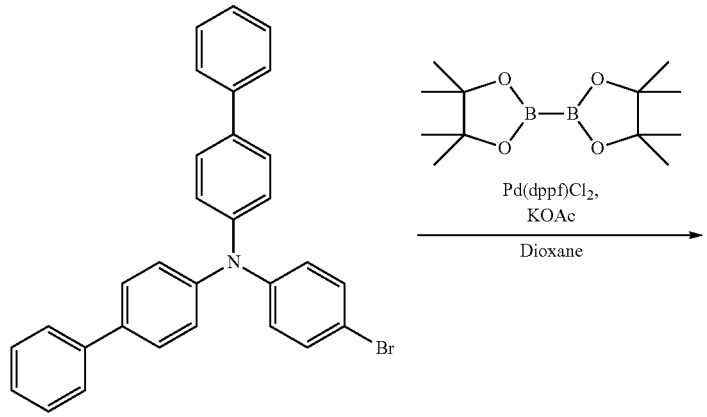
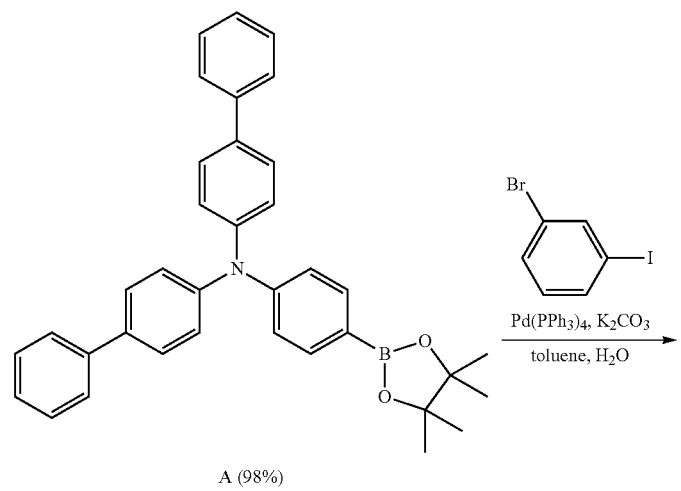
A (98%)
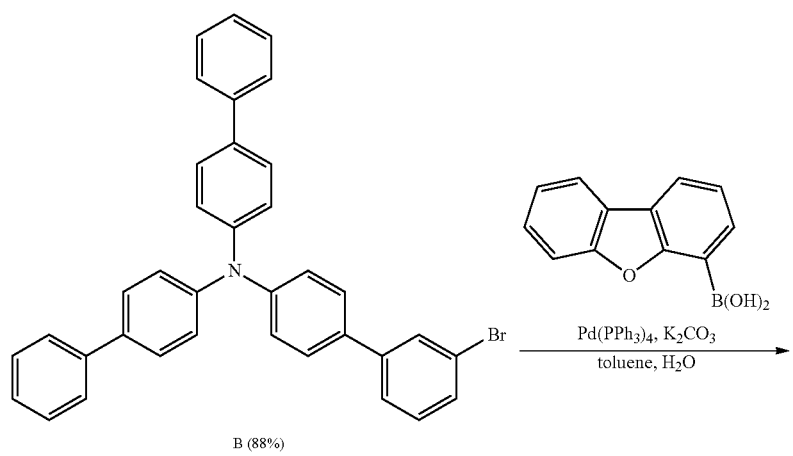
B (88%)

-continued

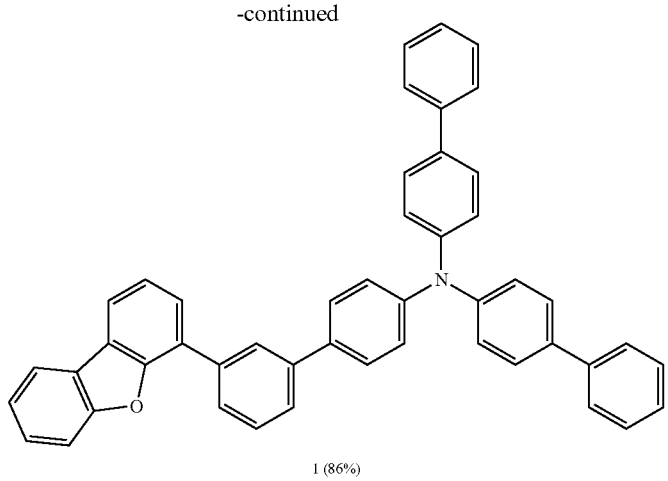

1 (86%)

Synthesis of Compound A

Under an Ar atmosphere, 53.8 g of N-[1,1'-biphenyl]-4-yl-N-(4-bromophenyl)-[1,1'-biphenyl]-4-amine, 6.46 g of Pd(dppf)Cl$_2$·CH$_2$Cl$_2$, 33.3 g of KOAc and 33.0 g of bis(pinacolato)diboron were added to a 2 L flask, followed by vacuum degassing in 750 mL of a dioxane solvent and stirring at about 100° C. for about 12 hours. Then, the solvents were distilled, CH$_2$Cl$_2$ and water were added, and an organic phase was separated. Magnesium sulfate and activated clay were added (e.g., to the organic phase), filtering with suction was performed, and solvents were distilled. The crude product thus obtained was separated by silica gel column chromatography (utilizing a mixture solvent of dichloromethane and hexane) to produce 56.8 g of Compound A as a white solid (Yield 98%). (FAB-MS: C$_{36}$H$_{34}$BNO$_2$, measured value: 523)

Synthesis of Compound B

Under an Ar atmosphere, 10.0 g of Compound A, 6.00 g of 1-iodo-3-bromobenzene, 1.54 g of Pd(PPh$_3$)$_4$, and 5.25 g of potassium carbonate were added to a 300 mL, three-necked flask, followed by heating and stirring in a mixture solvent of 450 mL of toluene and 60 mL of water at about 90° C. for about 8 hours. After air cooling, water was added, an organic layer was separated, and solvents were distilled. The crude product thus obtained was separated utilizing silica gel column chromatography (utilizing a mixture solvent of dichloromethane and hexane) and recrystallized utilizing a mixture solvent of toluene/hexane to produce 9.29 g of Compound B as a white solid (Yield 88%). (FAB-MS: C$_{36}$H$_{26}$BrN, measured value: 551)

Synthesis of Compound 1

Under an Ar atmosphere, 3.10 g of Compound B, 1.2 g of dibenzofuran-4-boronic acid, 0.84 g of Pd(PPh$_3$)$_4$, and 2.35 g of potassium carbonate were added to a 500 mL, three-necked flask, followed by heating and stirring in a mixture solvent of 170 mL of toluene and 80 mL of water at about 90° C. for about 8 hours. After air cooling, water was added, an organic layer was separated, and the solvents were distilled. The crude product thus obtained was separated utilizing silica gel column chromatography (utilizing a mixture solvent of dichloromethane and hexane) and recrystallized utilizing a mixture solvent of toluene/hexane to produce 3.08 g of Compound 1 as a white solid (Yield 86%). ($^1$H NMR (300 MHz, CDCl$_3$) 8.11 (s, 1H), 8.00 (d, J=7.6 Hz, 1H), 7.96 (d, J=7.6 Hz, 1H), 7.87 (d, J=7.4 Hz, 1H), 7.67-7.23 (m, 29H), FAB-MS: C$_{48}$H$_{33}$NO, measured value: 639)

The material for an organic EL device according to an embodiment may be synthesized, for example, as follows.

Synthesis of Compound 13

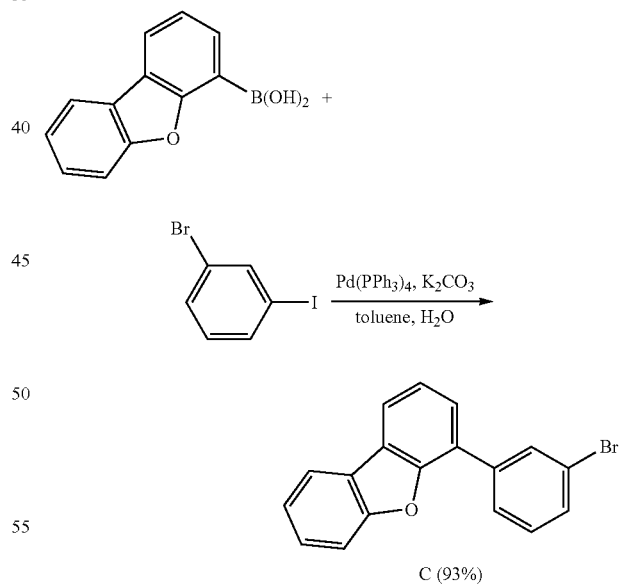

C (93%)

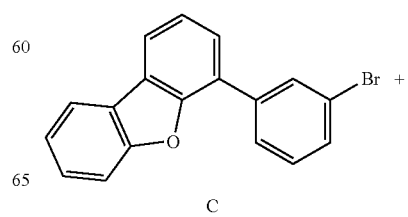

C

-continued

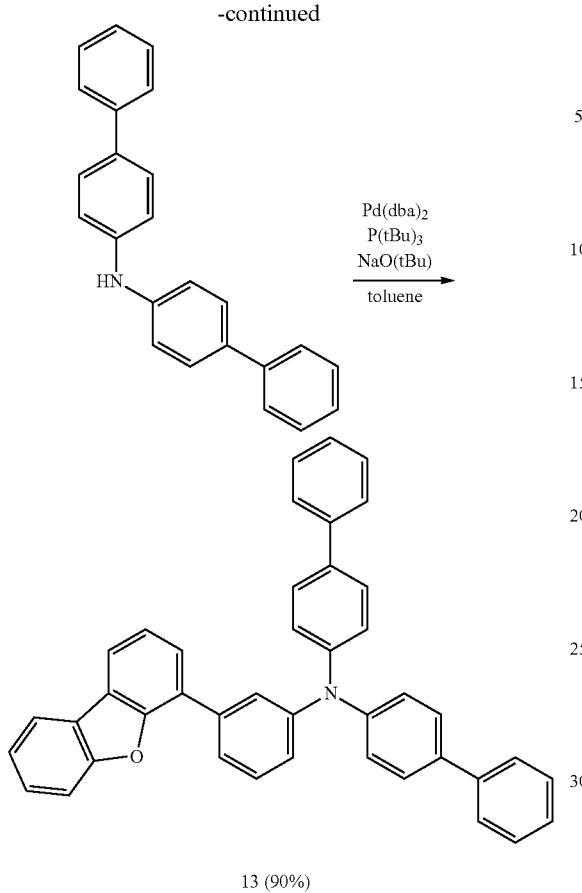

13 (90%)

Synthesis of Compound C

Under an Ar atmosphere, 10.0 g of dibenzofuran-4-boronic acid, 13.3 g of 1-iodo-3-bromobenzene, 5.45 g of Pd(PPh$_3$)$_4$, and 13.0 g of potassium carbonate were added to a 300 mL, three-necked flask, followed by heating and stirring in a mixture solvent of 300 mL of toluene and 90 mL of water at about 90° C. for about 8 hours. After air cooling, water was added, an organic layer was separated, and the solvents were distilled. The crude product thus obtained was separated utilizing silica gel column chromatography (utilizing a mixture solvent of dichloromethane and hexane) and recrystallized utilizing a mixture solvent of toluene/hexane to produce 14.1 g of Compound B as a white solid (Yield 93%). (FAB-MS: C$_{18}$H$_{11}$BrO, measured value: 322)

Synthesis of Compound 13

Under an Ar atmosphere, 2.00 g of Compound C, 1.99 g of bis(biphenylyl)amine, 0.18 g of bis(dibenzylideneacetone)palladium(O), 0.25 g of tri-tert-butylphosphine, and 0.89 g of sodium tert-butoxide were added to a 500 mL, three-necked flask, followed by heating and refluxing in 60 mL of a toluene solvent for about 4 hours. After air cooling, water was added, an organic layer was separated, and the solvents were distilled. The crude product thus obtained was separated utilizing silica gel column chromatography (toluene/hexane) to produce 3.14 g of Compound 13 as a white solid (Yield 90%). ($^1$H NMR (300MHz, CDCl$_3$) 7.96 (s, 1H), 7.83 (d, J=7.6 Hz, 1H), 7.80 (d, J=7.6 Hz, 1H), 7.70 (d, J=7.4 Hz, 1H), 7.67-7.23 (m, 25H), FAB-MS: C$_{42}$H$_{29}$NO, measured value: 563)

The material for an organic EL device represented by Formula 1 according to an embodiment may be synthesized, for example, as follows.

Synthesis of Compound 18

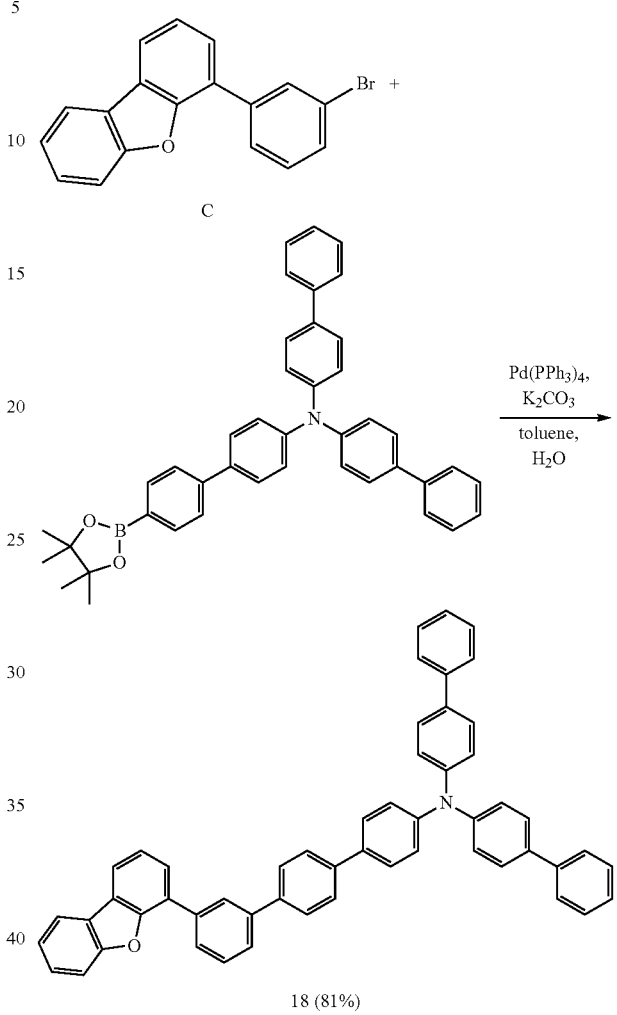

18 (81%)

Synthesis of Compound 18

Under an Ar atmosphere, 2.00 g of Compound C, 3.71 g of N,N-di([1,1'-biphenyl]-4-yl)-4'-(4,4,5,5-tetramethyl-1,3,2-dioxaborolan-2-yl)-[1,1'-biphenyl]-4-amine, 0.71 g of Pd(PPh$_3$)$_4$, and 1.71 g of potassium carbonate were added to a 500 mL, three-necked flask, followed by heating and stirring in a mixture solvent of 60 mL of toluene and 15 mL of water at about 90° C. for about 8 hours. After air cooling, water was added, an organic layer was separated, and the solvents were distilled.

The crude product thus obtained was separated by silica gel column chromatography (utilizing a mixture solvent of dichloromethane and hexane) and recrystallized utilizing a mixture solvent of toluene/hexane to produce 3.59 g of Compound 18 as a white solid (Yield 81%). ($^1$H NMR (300 MHz, CDCl$_3$) 8.08 (s, 1H), 8.01 (d, J=7.5 Hz, 1H), 7.93 (d, J=7.5 Hz, 1H), 7.82 (d, J=7.4 Hz, 1H), 7.75-7.25 (m, 33H), FAB-MS: C$_{54}$H$_{37}$NO, measured value: 715)

Organic EL devices according to Examples 1 to 3 were manufactured utilizing Compounds 1, 13 and 18 respectively as hole transport materials by the above-described manufacturing method.

1
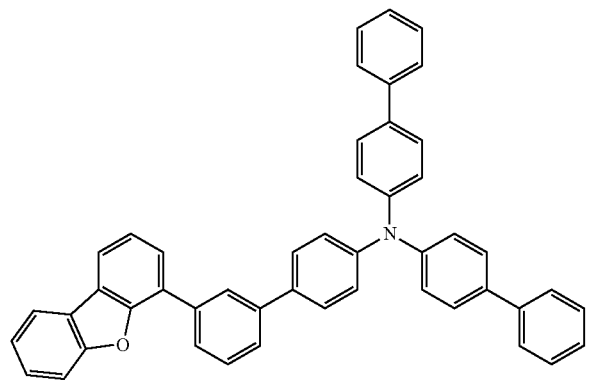
13
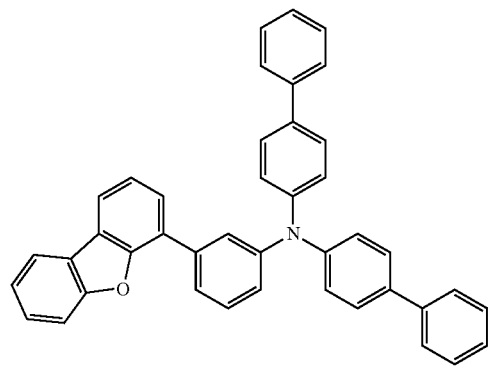
18
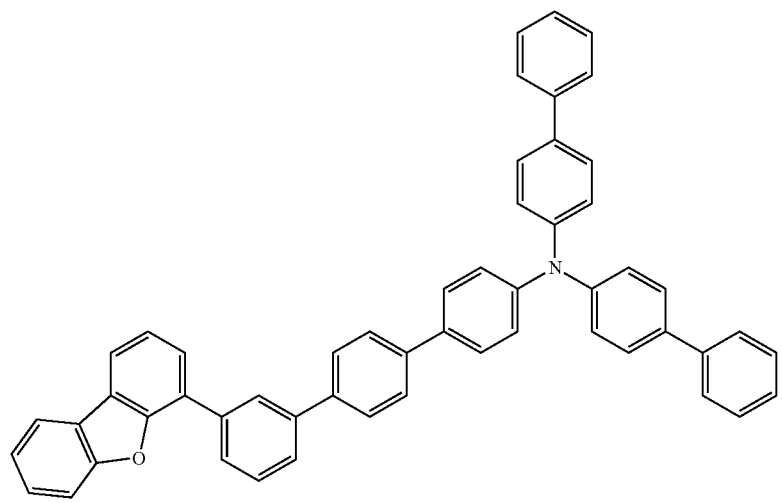
In addition, organic EL devices according to Comparative Examples 1 to 5 were manufactured utilizing the following Comparative Compounds C1 to C5 respectively as hole transport materials.
C1
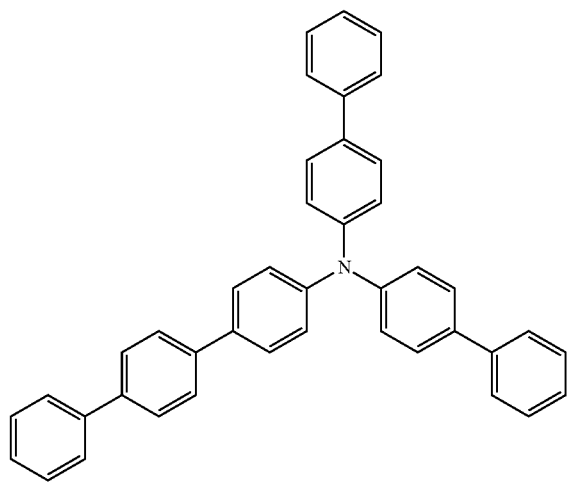
-continued
C2
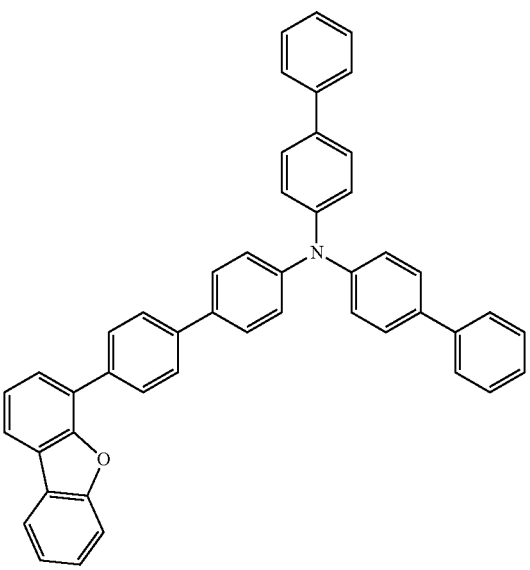

C3

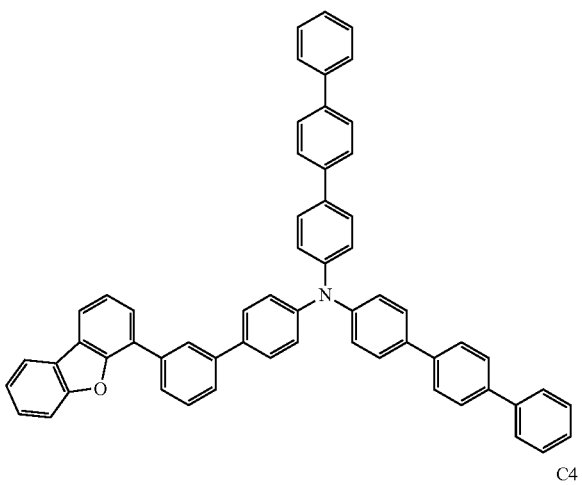

C4

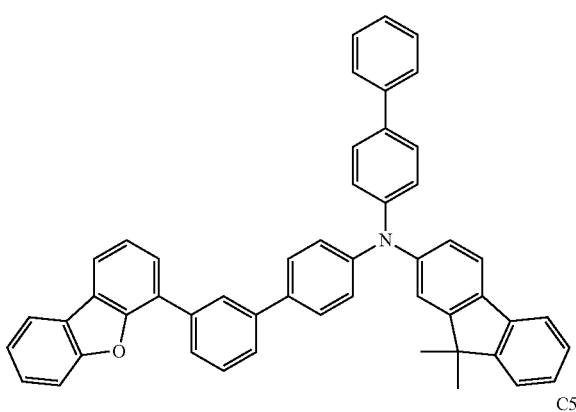

C5

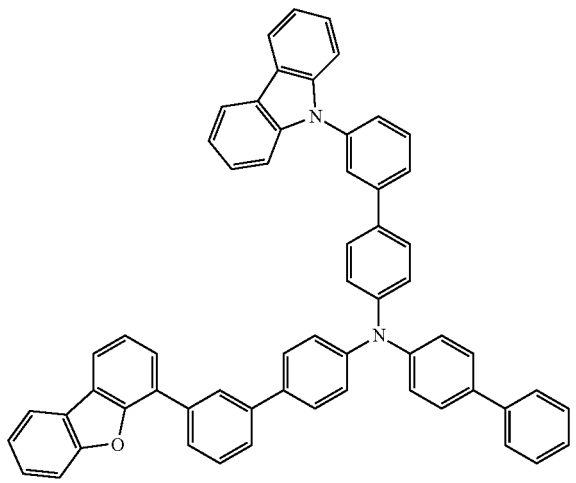

Figure 2:
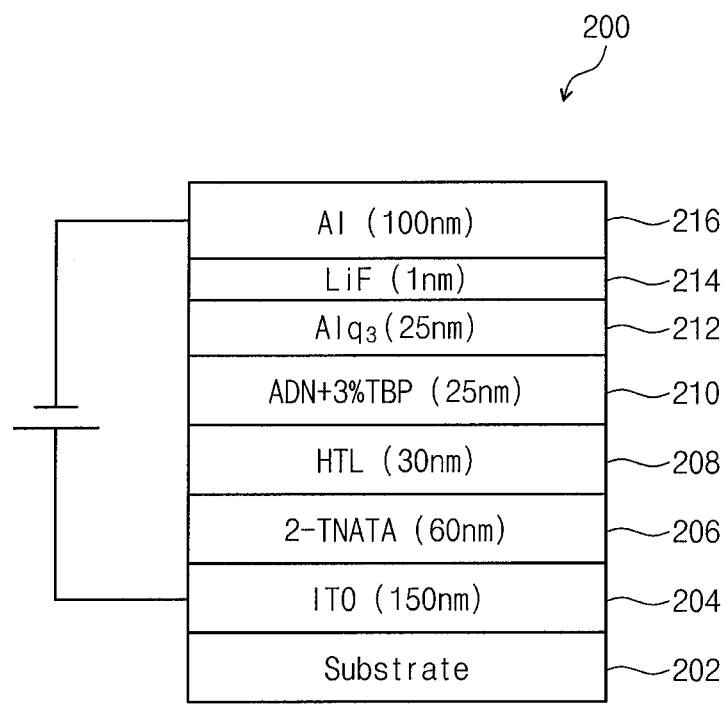
FIG. 2 is a schematic diagram of an organic EL device 200 according to an embodiment of the inventive concept.

The organic EL device 200 according to an embodiment is shown in FIG. 2. In this embodiment, the substrate 202 was formed utilizing a transparent glass substrate, the anode 204 was formed utilizing ITO to a thickness of about 150 nm, the hole injection layer 206 was formed utilizing 2-TNATA to a thickness of about 60 nm, the hole transport layer 208 was formed to a thickness of about 30 nm, the emission layer 210 was formed utilizing ADN doped with 3% TBP to a thickness of about 25 nm, the electron transport layer 212 was formed utilizing $Alq_3$ to a thickness of about 25 nm, the electron injection layer 214 was formed utilizing LiF to a thickness of about 1 nm, and the cathode 216 was formed utilizing Al to a thickness of about 100 nm.

With respect to the organic EL devices 200 thus manufactured, driving voltages, emission efficiency and half-life were evaluated. Current density is a value at about 10 $mA/cm^2$, and half-life refers to the time period required for decreasing the luminance to half from an initial luminance of about 1,000 $cd/m^2$. The evaluation results are shown in the following Table 1.

TABLE 1

| Device manufacturing example | Hole transport material | Voltage (V) | Emission efficiency (cd/A) | Life LT50 (h) |
|---|---|---|---|---|
| Example 1 | Compound 1 | 6.2 | 6.8 | 2,800 |
| Example 2 | Compound 13 | 6.2 | 6.5 | 2,000 |
| Example 3 | Compound 18 | 6.4 | 7.0 | 2,300 |
| Comparative Example 1 | Compound C1 | 6.3 | 5.2 | 1,400 |
| Comparative Example 2 | Compound C2 | 6.6 | 6.1 | 1,100 |
| Comparative Example 3 | Compound C3 | 6.2 | 6.3 | 1,800 |
| Comparative Example 4 | Compound C4 | 6.3 | 6.2 | 1,800 |
| Comparative Example 5 | Compound C5 | 6.7 | 5.6 | 1,800 |

Referring to the results in Table 1, the organic EL devices utilizing the materials for an organic EL device represented by Formula 1 as hole transport materials showed higher emission efficiency and longer life than those of the organic EL devices utilizing the comparative compounds.

If comparing Example 1 with Comparative Example 1, long life and high efficiency was realized in the organic EL device according to Example 1, because dibenzofuran was introduced at the meta position of a phenylene group combining with an amine group, and the properties of the amine were maintained, polarization in a molecule was generated due to the effect of the oxygen atom of the dibenzofuran, and amorphous properties were improved.

If comparing Example 1 with Comparative Example 2, dibenzofuran was combined at the para position of a phenylene group combining with an amine group, and a conjugation structure of the dibenzofuran and the amine was formed in Comparative Example 2. Thus, the stability of radicals was deteriorated, and so, life (e.g., lifespan) was decreased.

In Comparative Example 3, a terphenyl group was introduced in the amine group, then crystallinity of a material was improved, and the amorphous properties were deteriorated, and also life (e.g., lifespan) was decreased.

The emission efficiency for Example 1 was improved when compared to that of Comparative Example 4. This result would be obtained by substituting a fluorenyl group with a biphenyl group, and the distance between molecules was decreased and the charge mobility was improved. In addition, life was improved for Example 1 when compared to that of Comparative Example 5. This result would be obtained by introducing a carbazolyl group to the amine group, and the whole molecule has a twisted structure, thereby deteriorating the layer quality in Compound C5 of Comparative Example 5.

In addition, the life for Example 2 was shorter when compared to that for Examples 1 and 3, because an m-phenylene group was directly combined with a nitrogen atom in the amine, and the diffusion of electrons of the amine was restricted and the radicals were not stabilized.

In the material for an organic EL device represented by Formula 1 according to an embodiment of the inventive concept, dibenzofuran is introduced at the meta position of a phenylene group combining with an amine group, and the amorphous properties of the material may be improved. Thus, charge mobility may be increased, and long life and high emission efficiency may be realized. In addition, since the material for an organic EL device according to an embodiment has a wide energy gap, application thereof in from a green emission region to a red emission region may be possible.

According to the inventive concept, a material for an organic EL device realizing high efficiency and long life and an organic EL device including the same may be provided. Particularly, a material for an organic EL device represented by Formula 1 realizing high efficiency and long life in a blue emission region, utilized in at least one layer of stacking layers disposed between an emission layer and an anode, and an organic EL device including the same may be provided. In the material for an organic EL device according to an embodiment, dibenzofuran is introduced at the meta position of a phenylene group combining with a nitrogen atom (N) of an amine group directly or via a linker (L), the amorphous properties may be improved, charge mobility may be increased, and long life and high emission efficiency may be realized.

Expressions such as "at least one of," when preceding a list of elements, modify the entire list of elements and do not modify the individual elements of the list. Further, the use of "may" when describing embodiments of the inventive concept refers to "one or more embodiments of the inventive concept." Also, the term "exemplary" is intended to refer to an example or illustration.

As used herein, the term "substantially," "about," and similar terms are used as terms of approximation and not as terms of degree, and are intended to account for the inherent deviations in measured or calculated values that would be recognized by those of ordinary skill in the art. Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

The above-disclosed subject matter is to be considered illustrative and not restrictive, and the appended claims are intended to cover all such modifications, enhancements, and other embodiments, which fall within the true spirit and scope of the inventive concept. Thus, to the maximum extent allowed by law, the scope of the inventive concept is to be determined by the broadest permissible interpretation of the following claims and their equivalents, and shall not be restricted or limited by the foregoing detailed description.

What is claimed is:

1. A material for an organic electroluminescent (EL) device, the material being one selected from the group consisting of compounds 1 to 22:

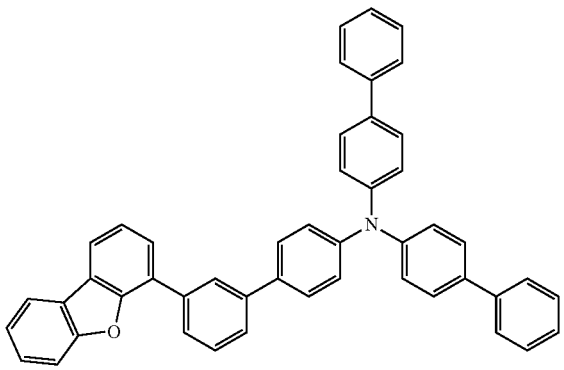

1

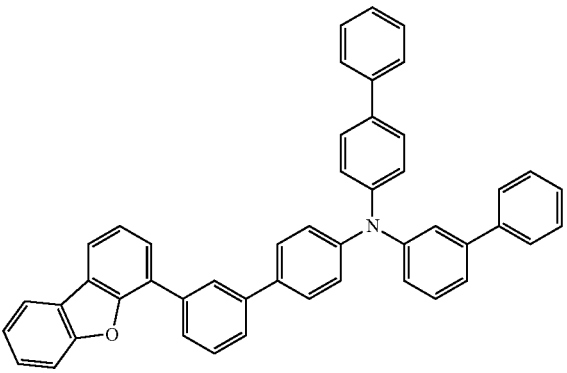

2

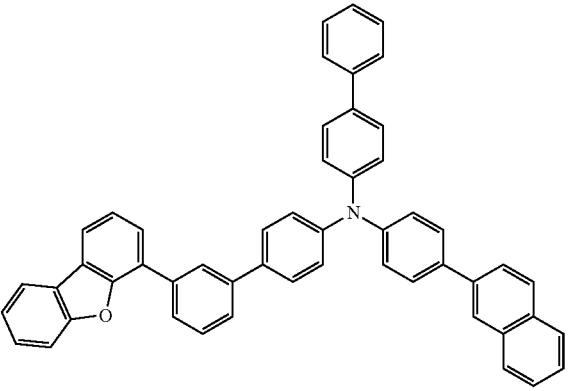

3

4
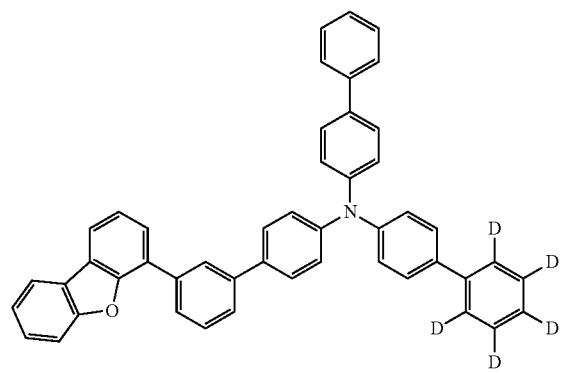
5
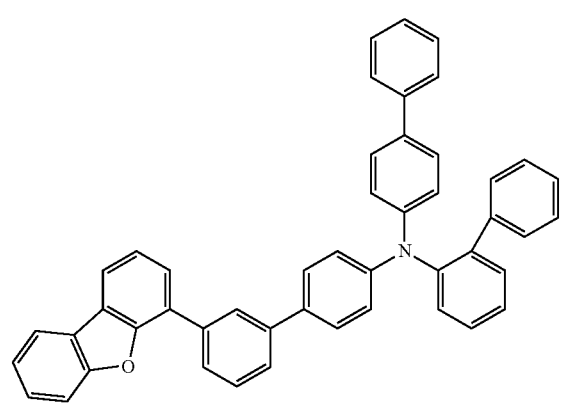
6
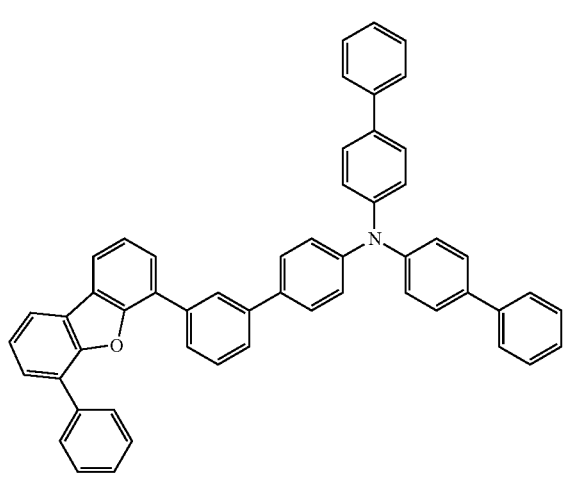
7
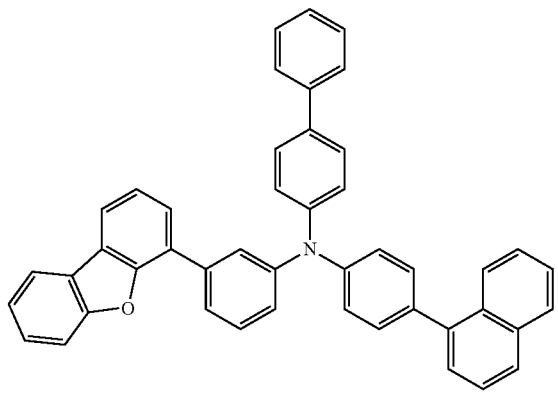
8
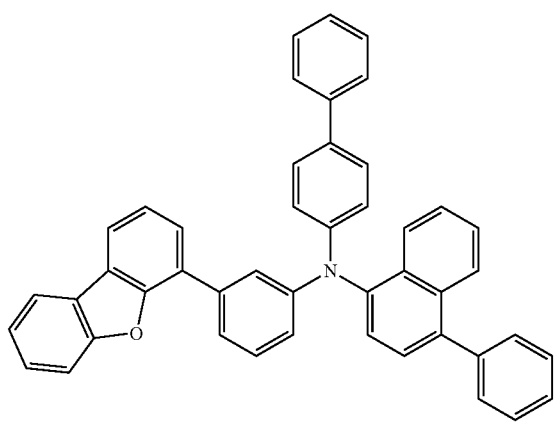
9
10

11
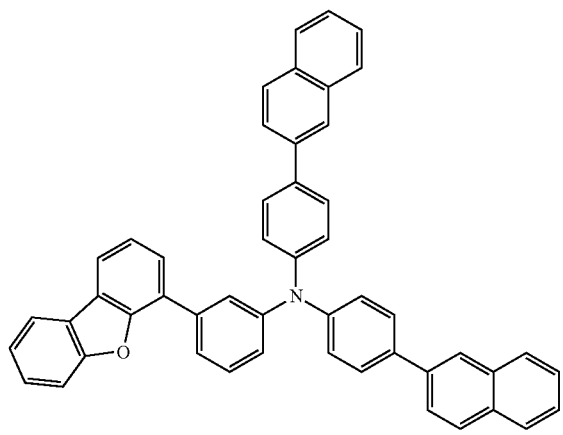
12
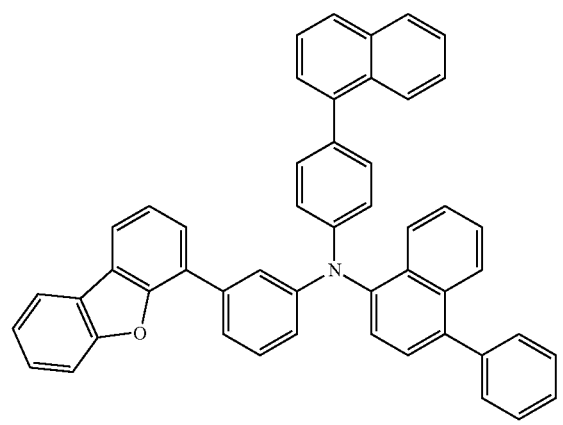
13
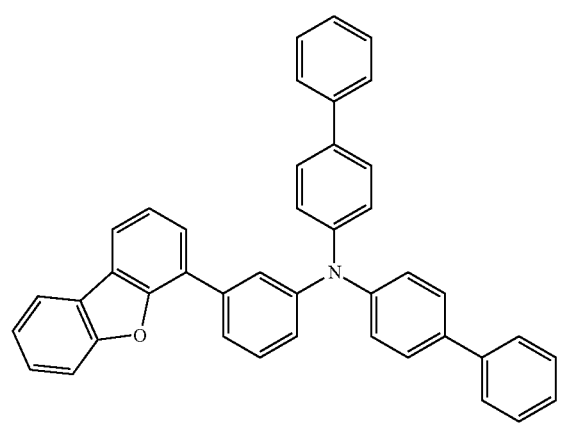
14
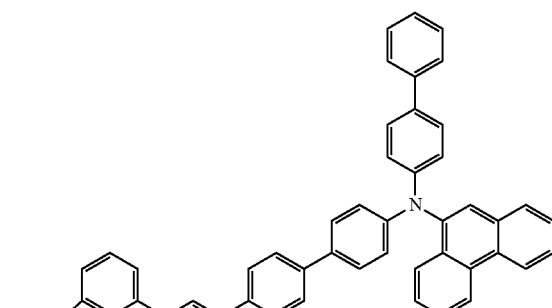
15
16
17
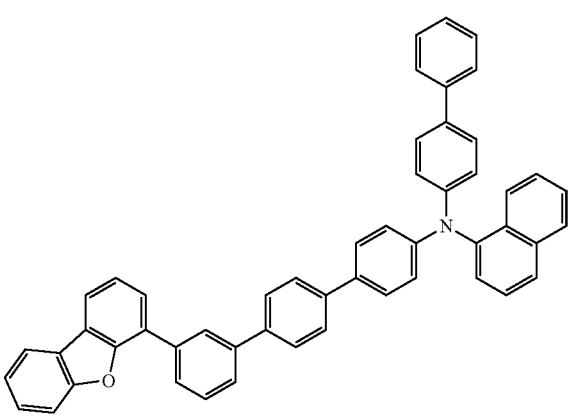

18
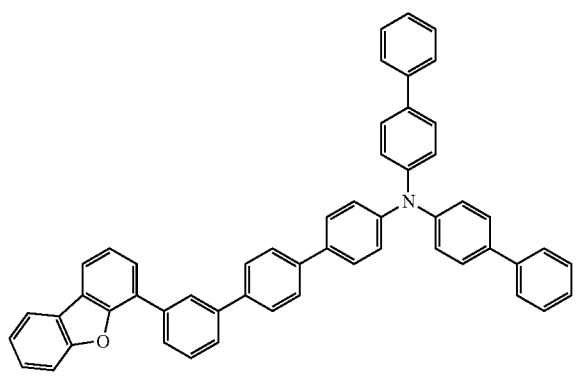
19
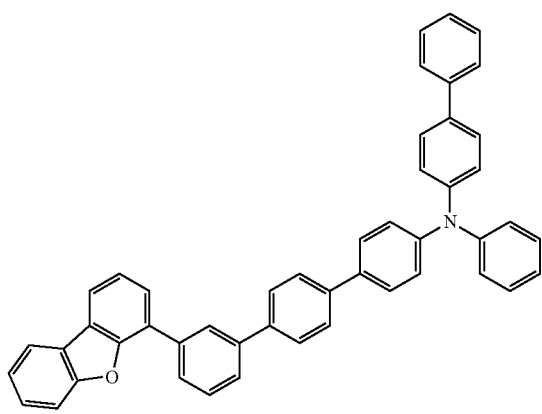
20
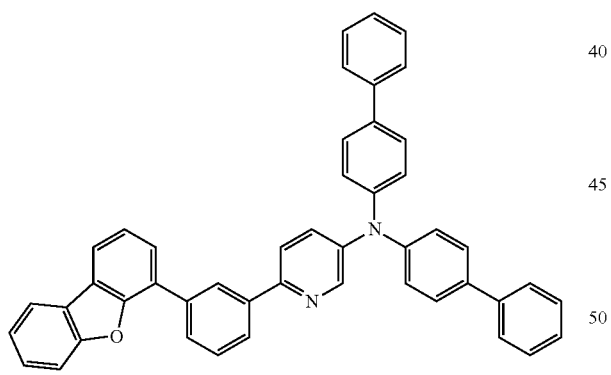
21
22
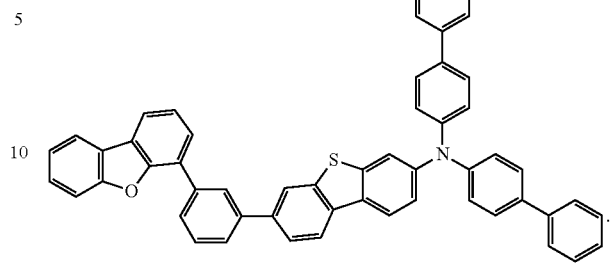
2. The material for an organic EL device of claim 1, wherein the material represented by Formula 1 is one selected from the group consisting of compounds 1 to 6:
1
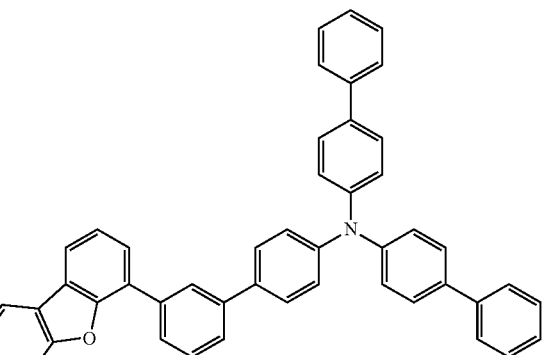
2
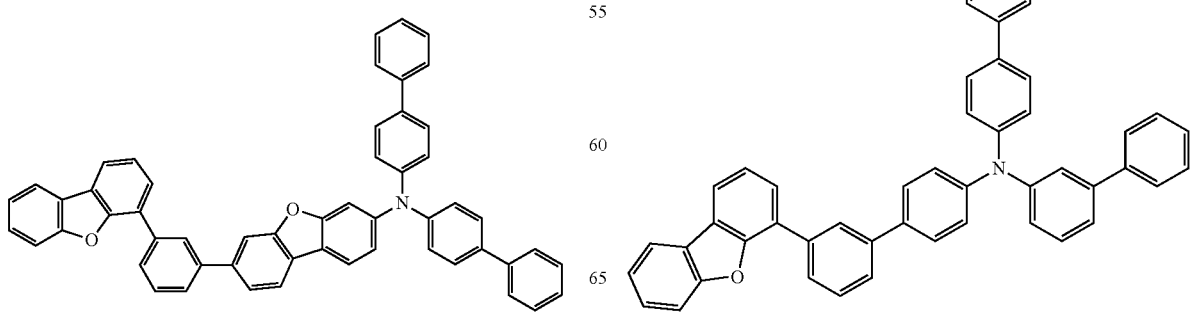

3
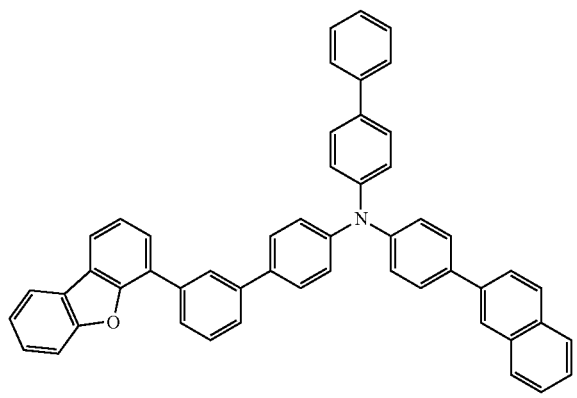
6
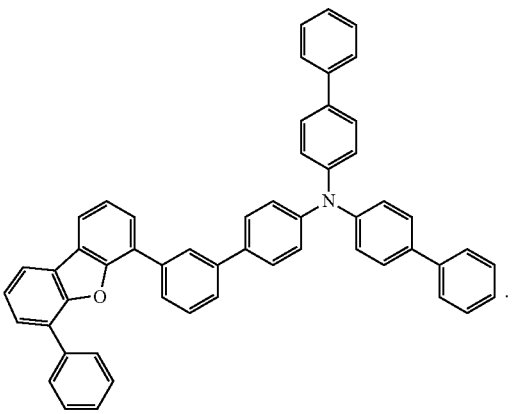
3. The material for an organic EL device of claim 1, wherein the material represented by Formula 1 is one selected from the group consisting of compounds 7 to 12:
4
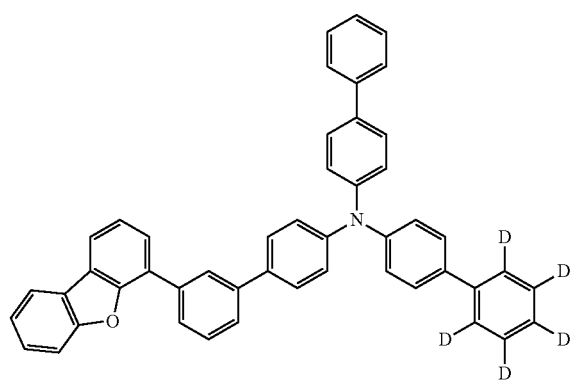
7
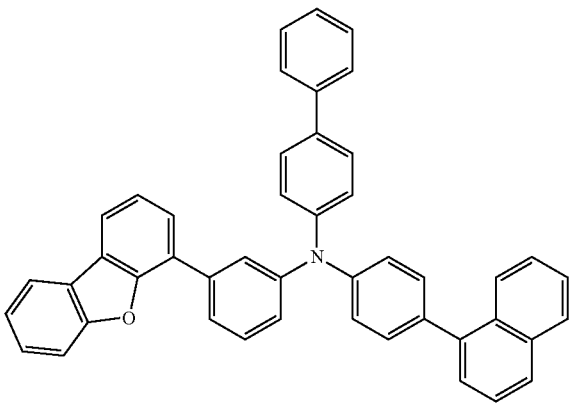
5
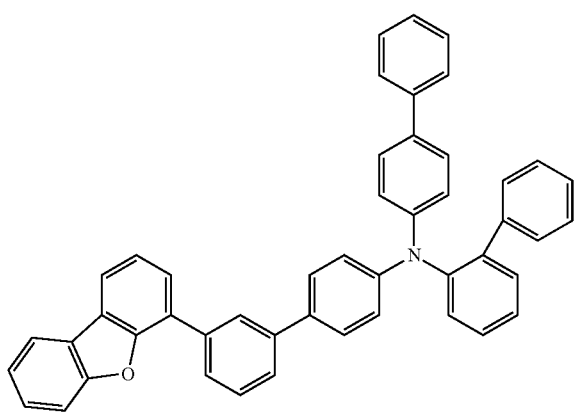
8
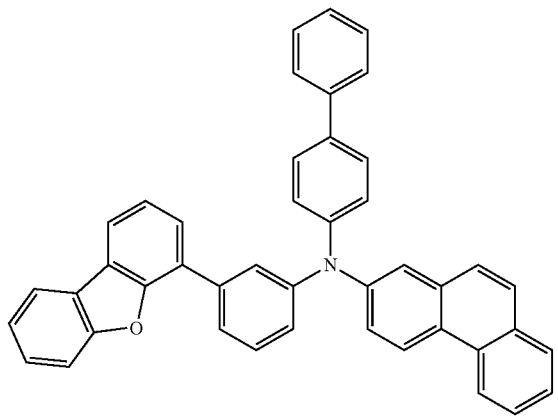

9
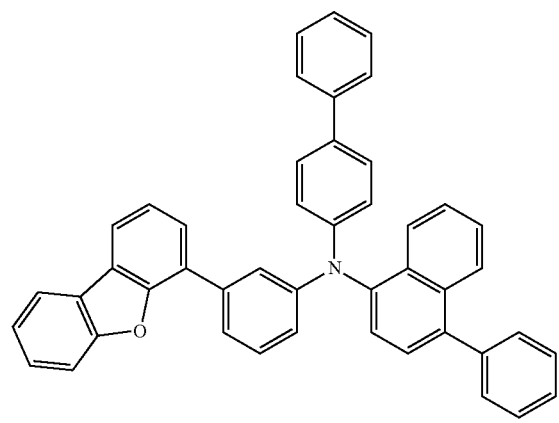
10
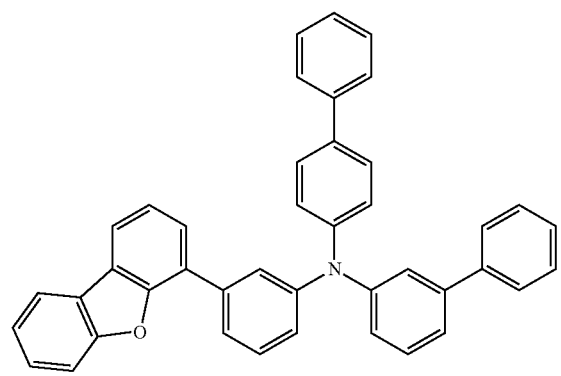
11
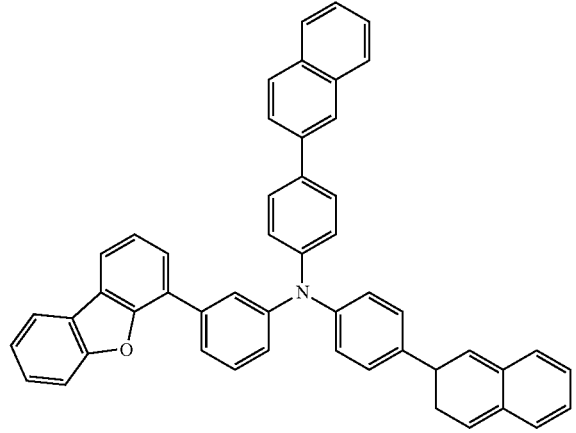
12
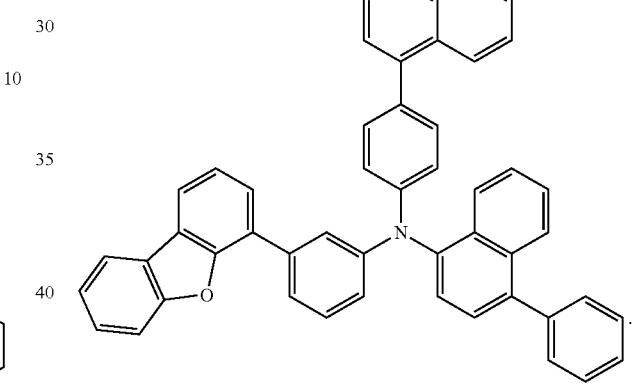
4. The material for an organic EL device of claim 1, wherein the material represented by Formula 1 is one selected from the group consisting of compounds 13-19:
13
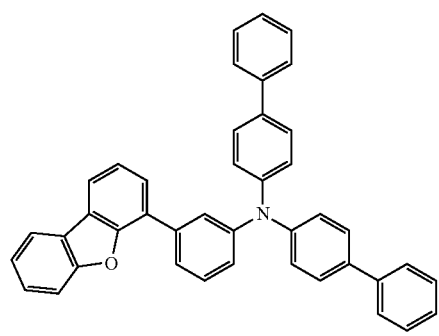
14
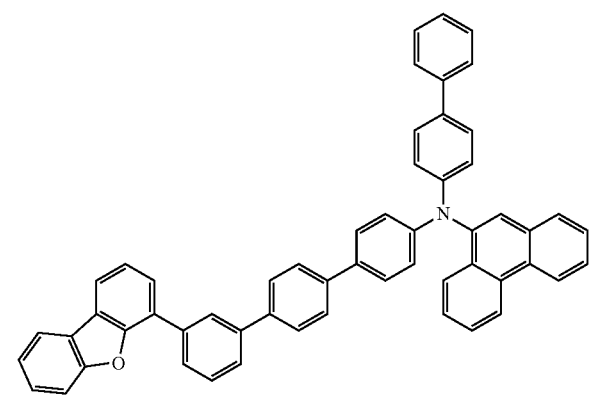

15
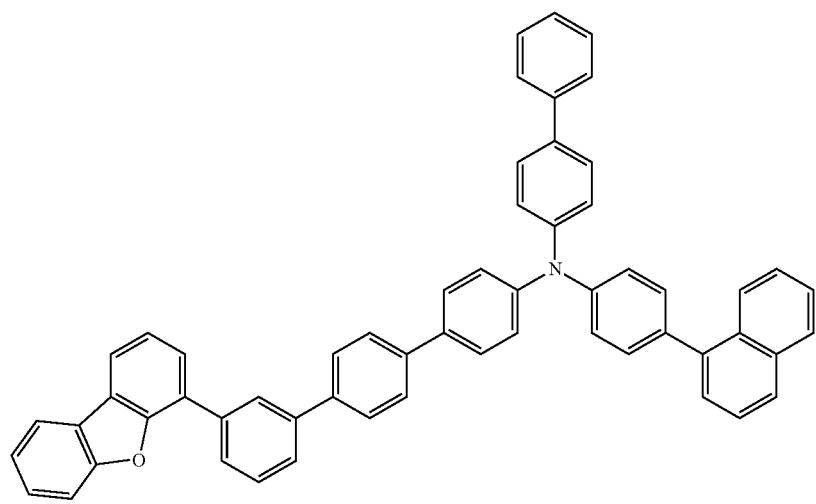
16
17
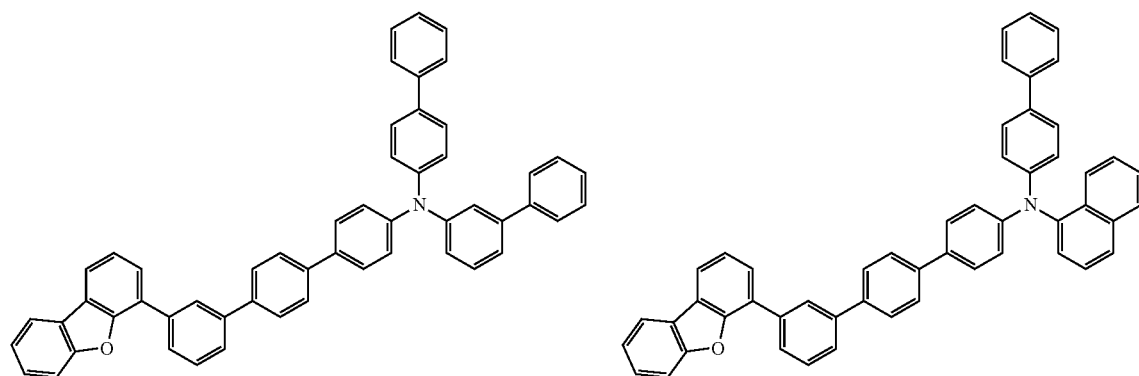
18
19
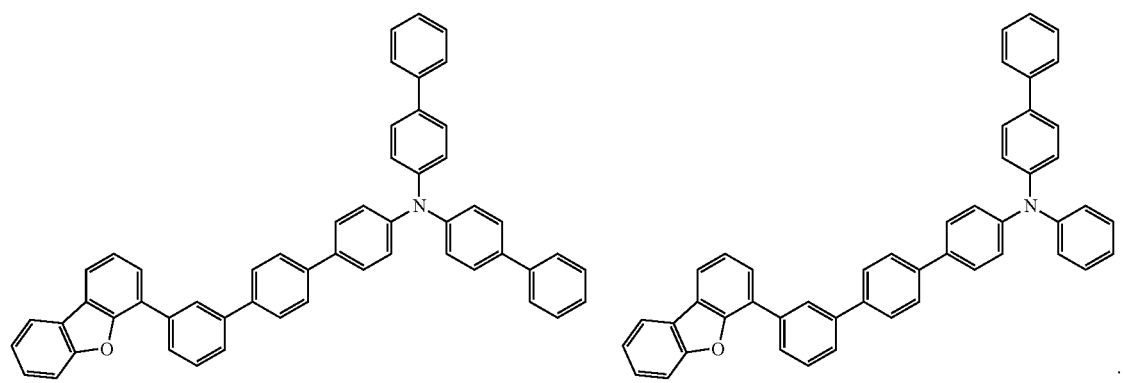

5. The material for an organic EL device of claim 1, wherein the material represented by Formula 1 is one selected from the group consisting of compounds 20 to 22:
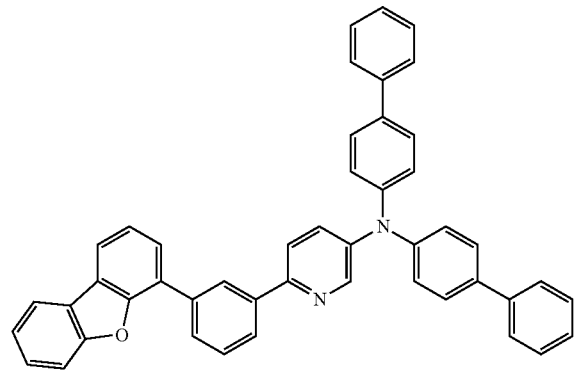
20
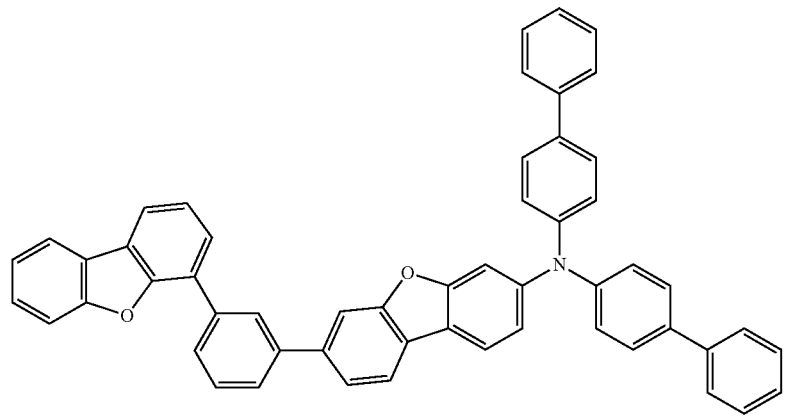
21
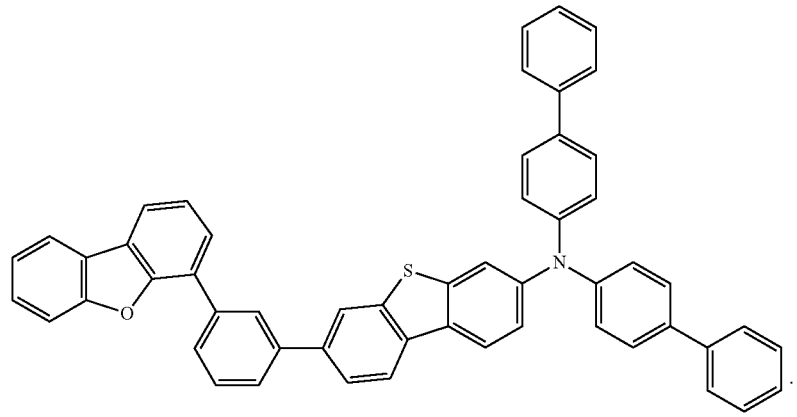
22

6. An organic electroluminescent (EL) device comprising:
an anode;
an emission layer on the anode; and
a plurality of stacking layers between the anode and the emission layer,
wherein at least one of the plurality of stacking layers comprises a material for an organic EL device, the material being selected from the group consisting of compounds 1 to 22:
1
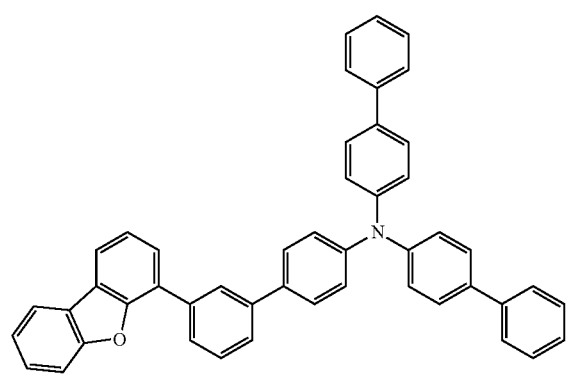
2
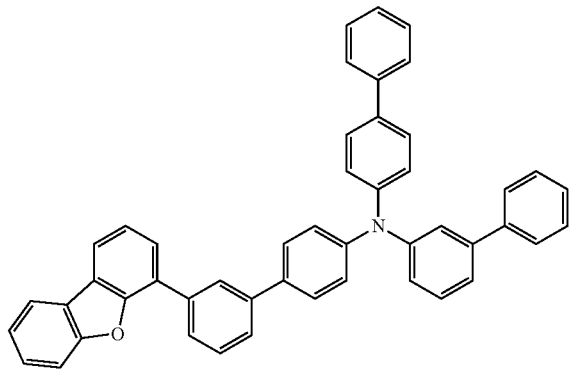
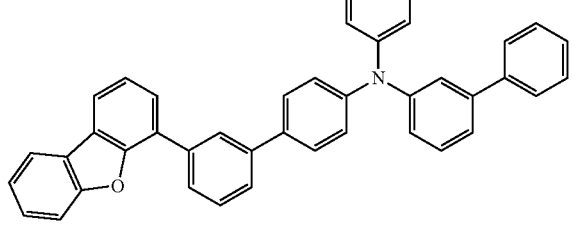
3
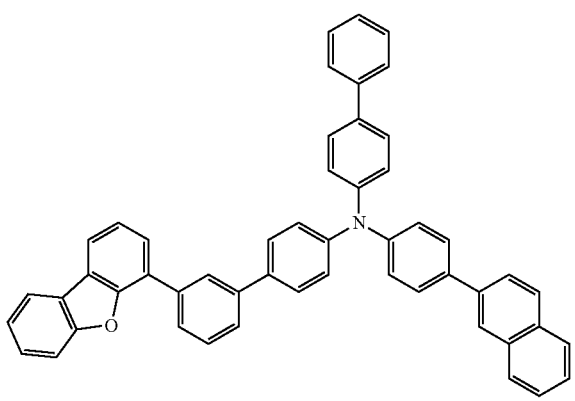
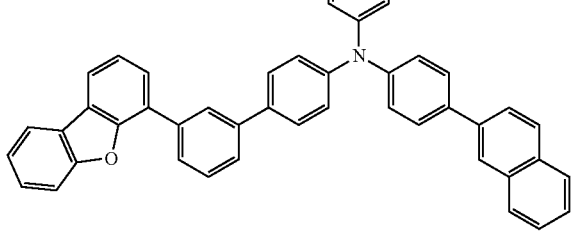
4
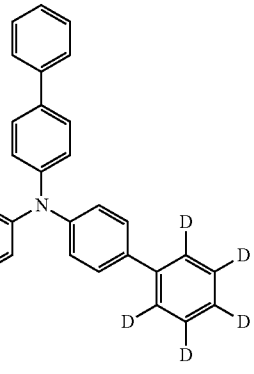
5
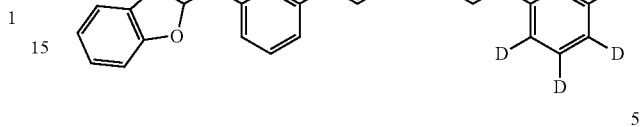
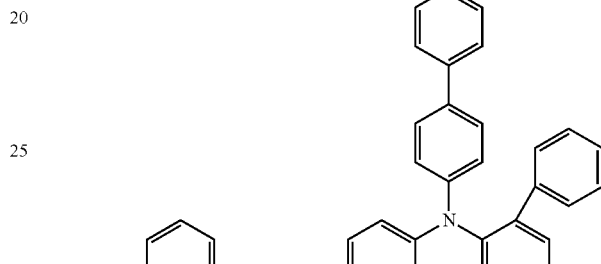
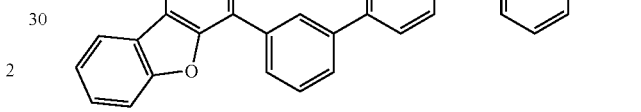
6
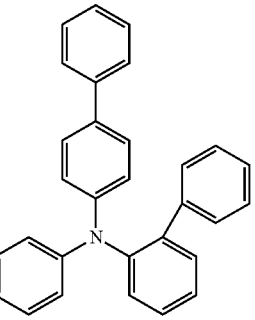
7
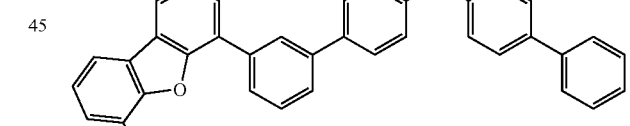
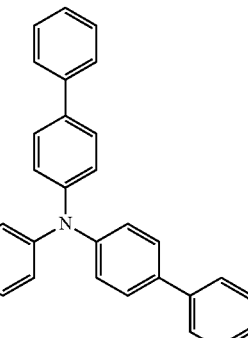

8
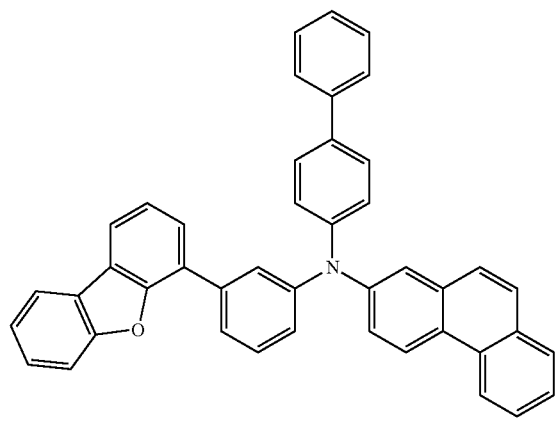
9
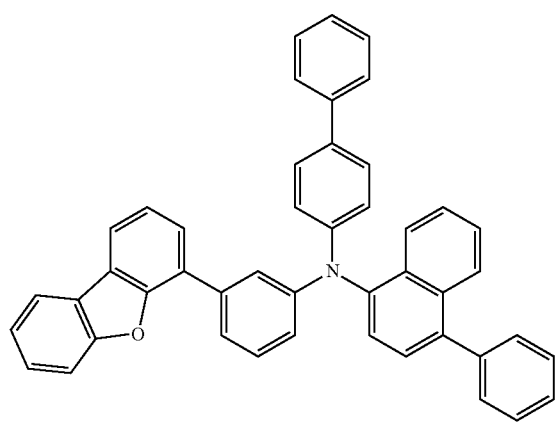
10
11
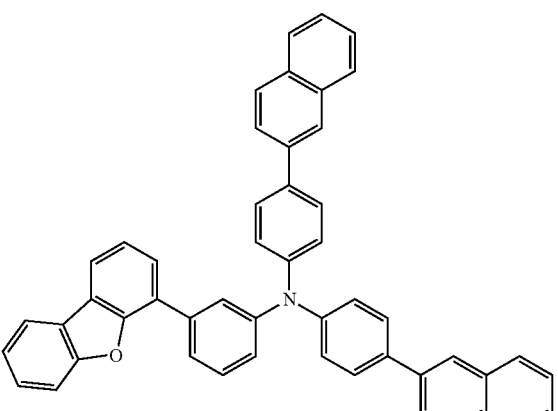
12
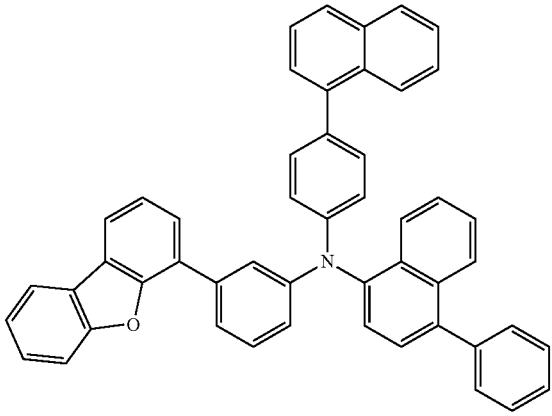
13
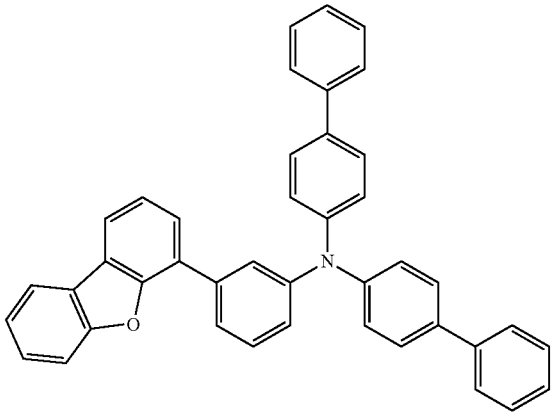

14
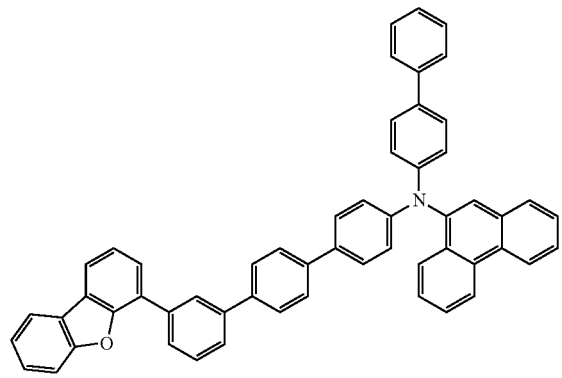
15
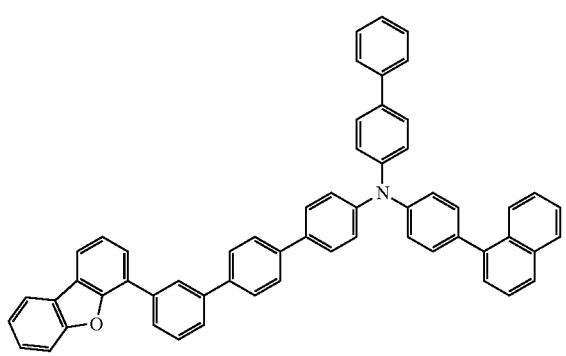
16
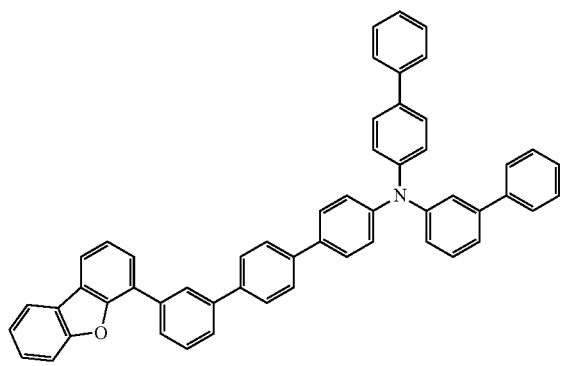
17
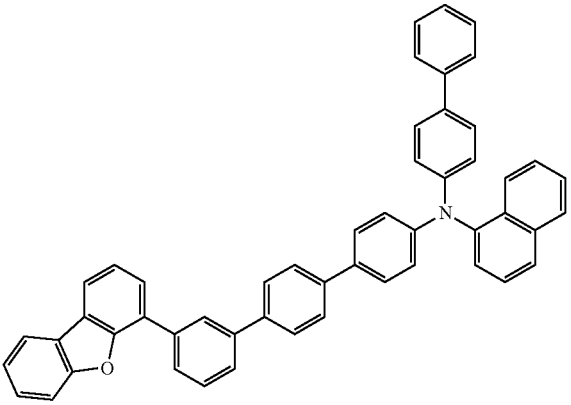
18
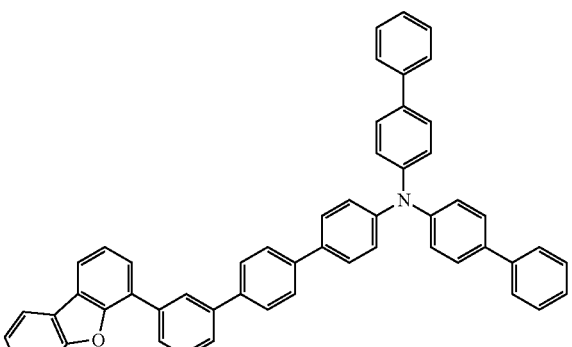
19
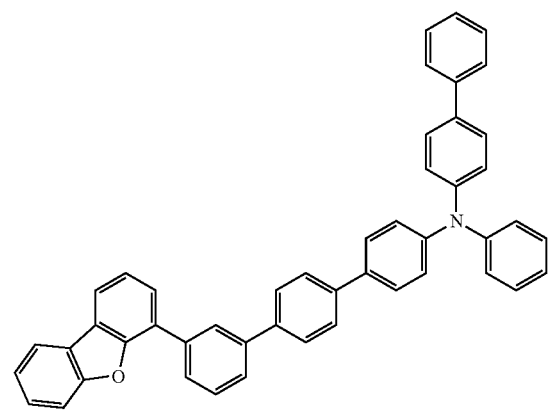
20
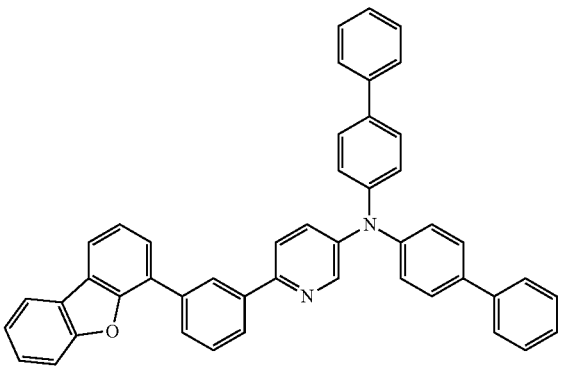
21
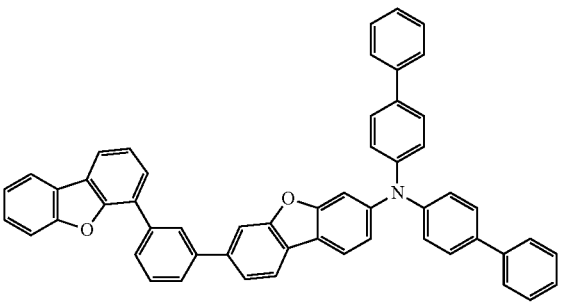

22
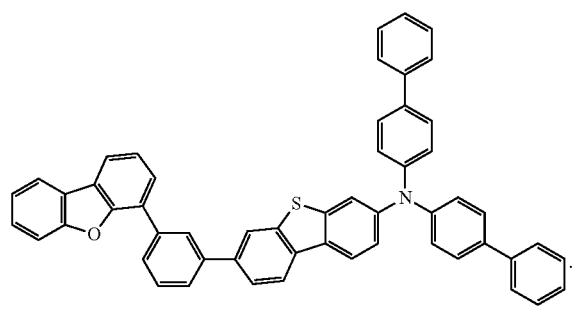
7. The organic EL device of claim 6, wherein the plurality of stacking layers comprises a hole transport layer, and
wherein the hole transport layer comprises the material selected from the group consisting of the compounds 1 to 22.
8. The organic EL device of claim 6, wherein the material represented by Formula 1 is one selected from the group consisting of compounds 1 to 6:
1
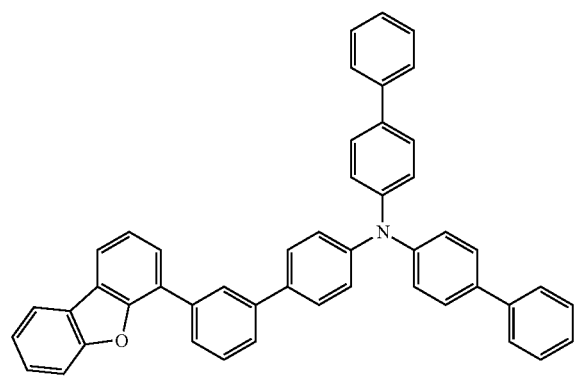
2
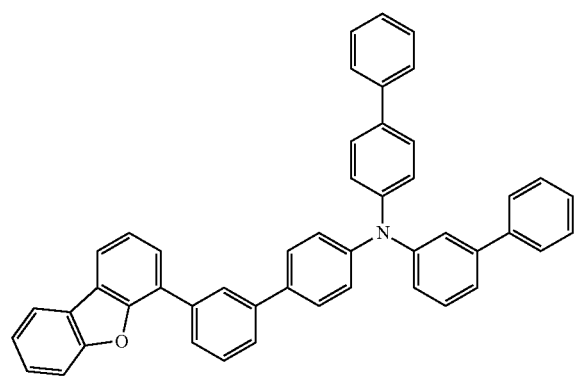
3
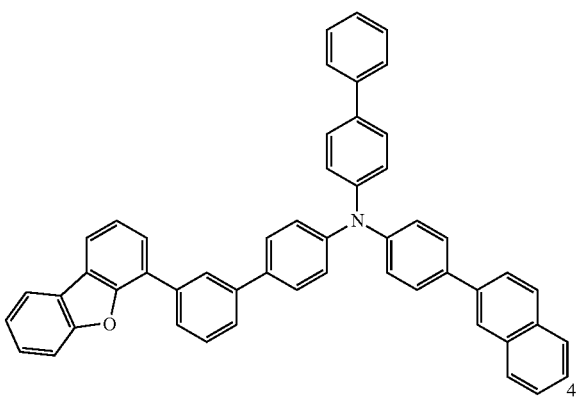
4
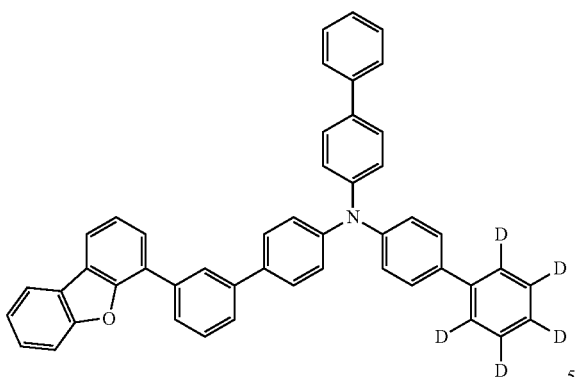
5
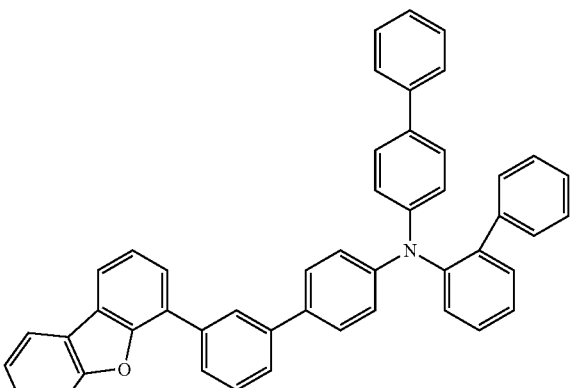
6
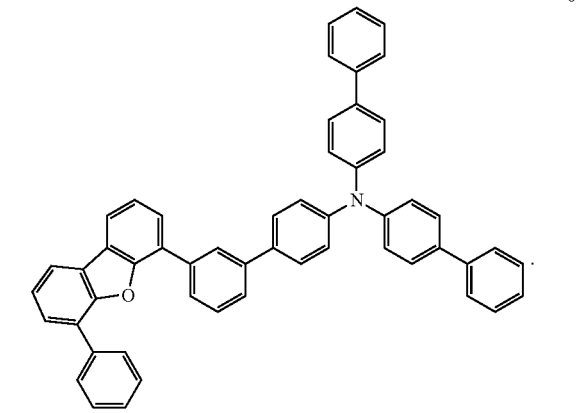

9. The organic EL device of claim 6, wherein the material represented by Formula 1 is one selected from the group consisting of compounds 7 to 12:
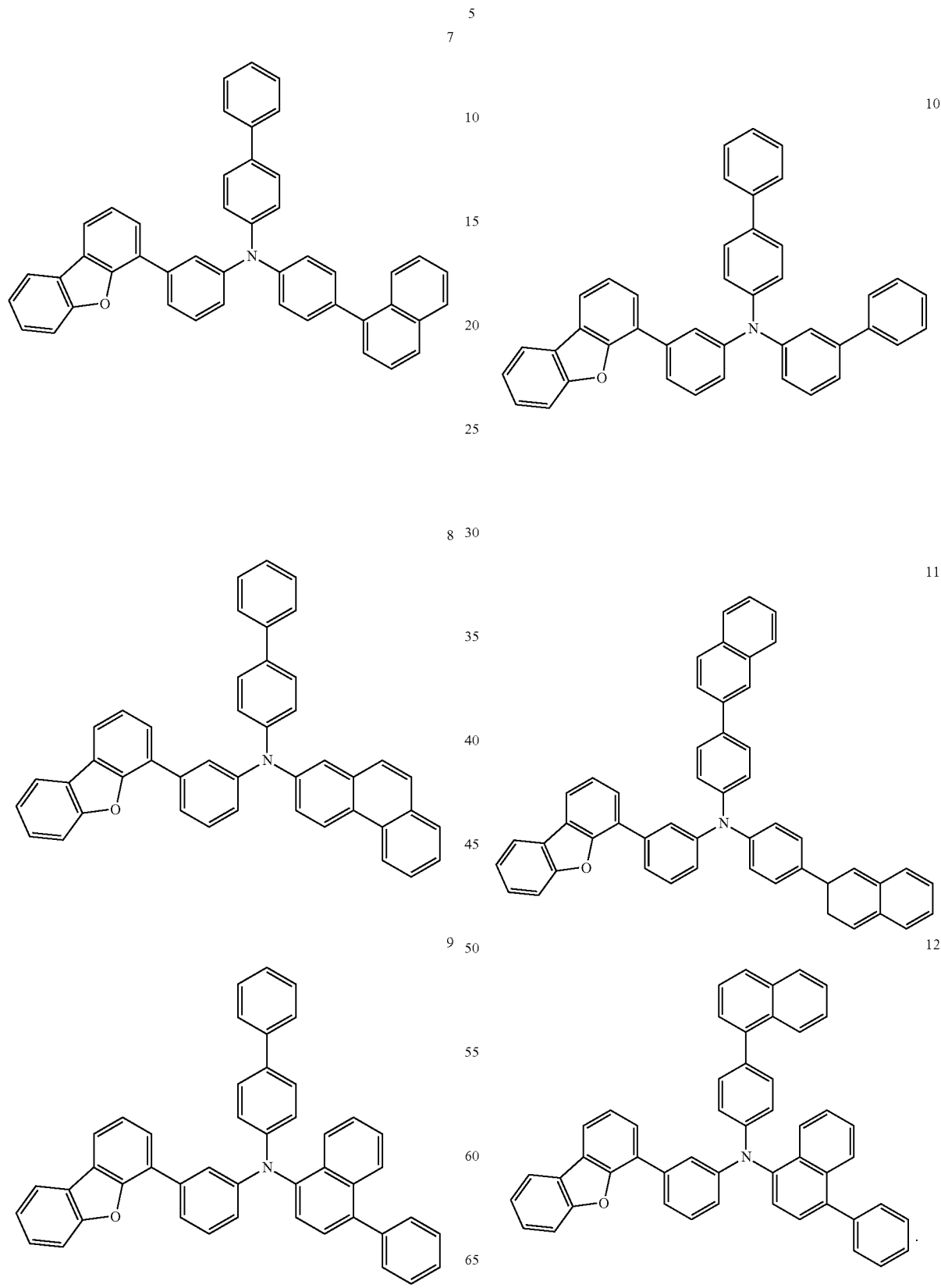

10. The organic EL device of claim 6, wherein the material represented by Formula 1 is one selected from the group consisting of compounds 13 to 19:
13
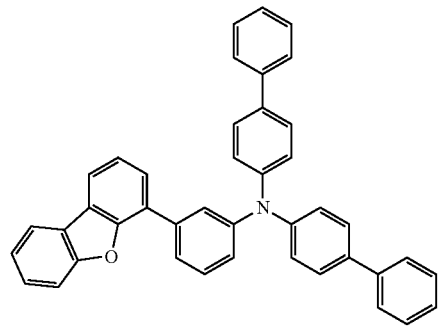
14
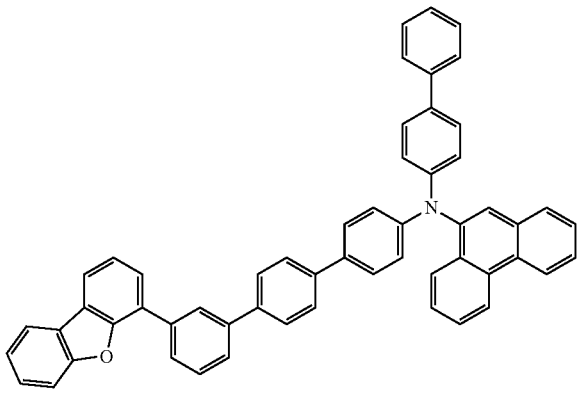
15
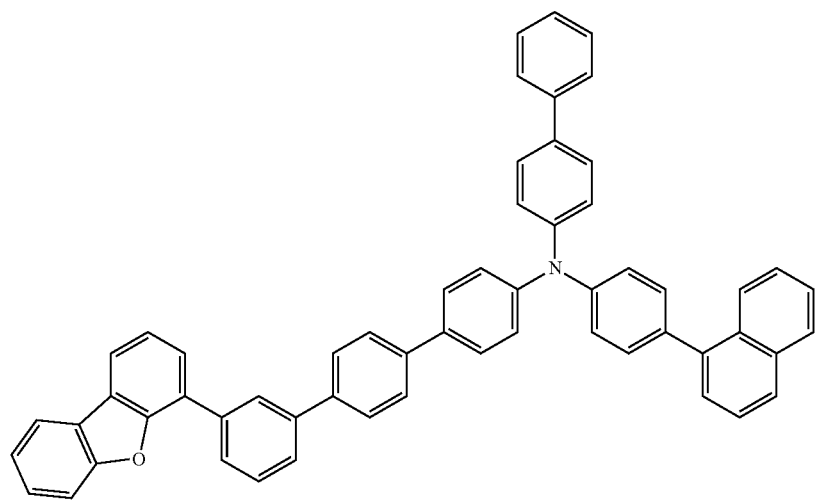
16
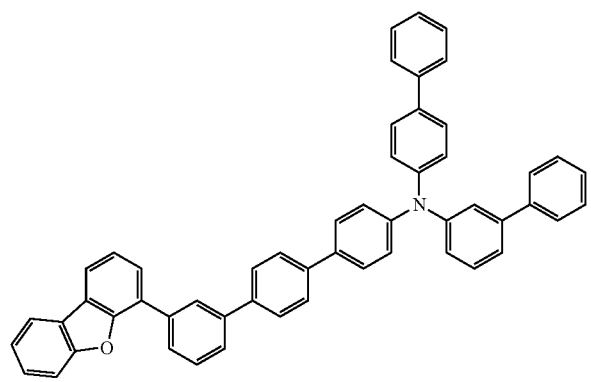
17
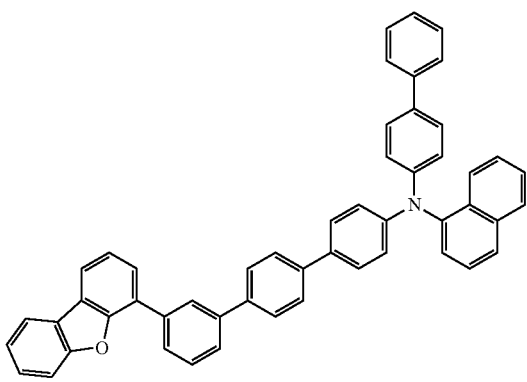

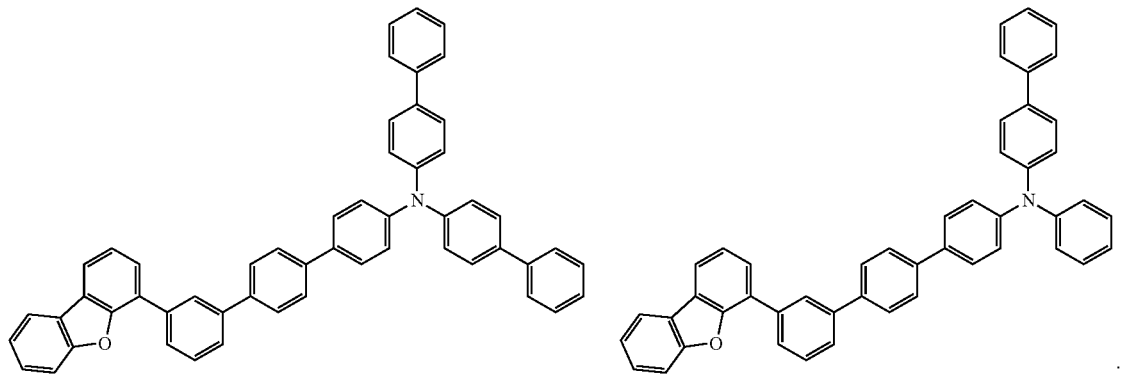
11. The organic EL device of claim 6, wherein the material represented by Formula 1 is one selected from the group consisting of compounds 20 to 22:
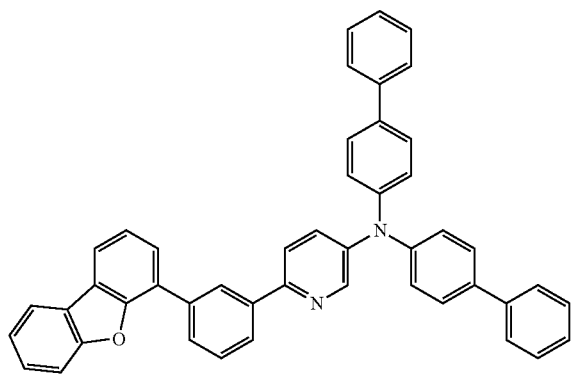
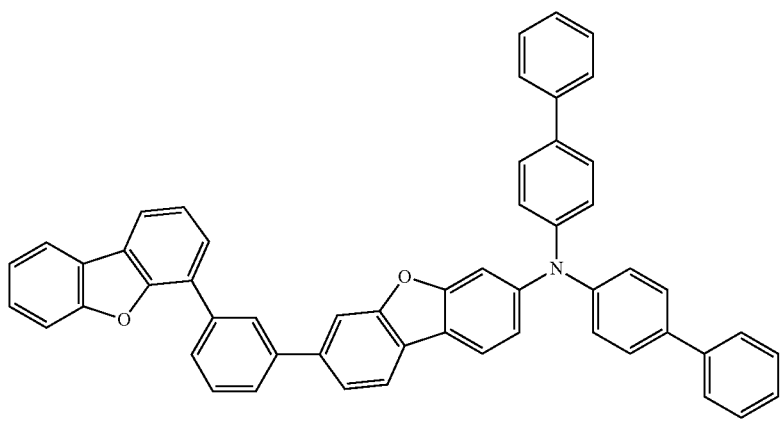

-continued
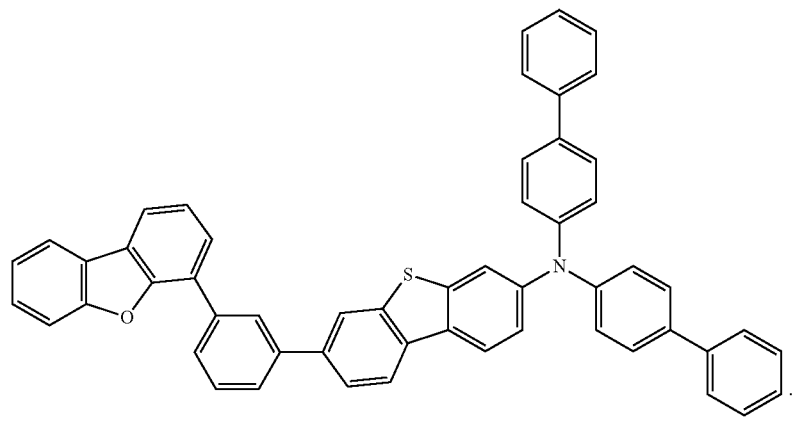
22
12. An organic electroluminescent (EL) device comprising:
    an anode;
    an emission layer on the anode; and
    a plurality of stacking layers between the anode and the emission layer,
    wherein the emission layer comprises a material selected from the group consisting of compounds 1 to 22:
-continued
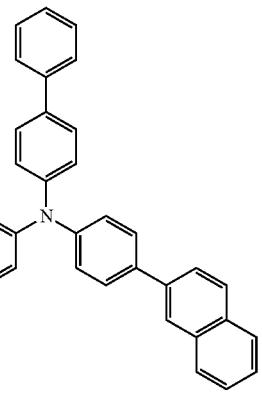
3
1
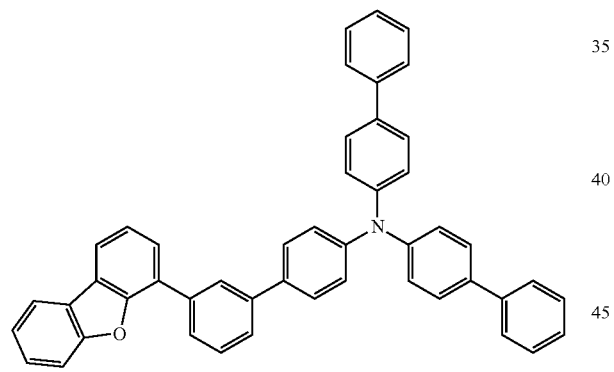
2
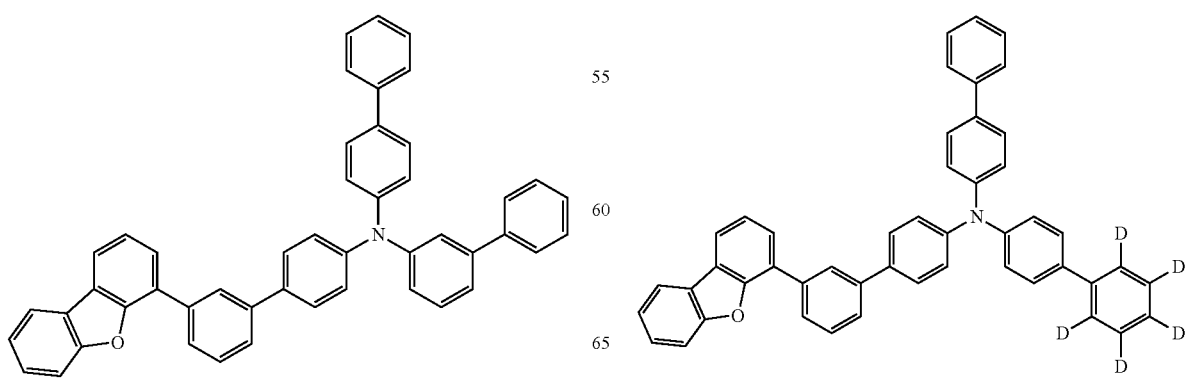
4

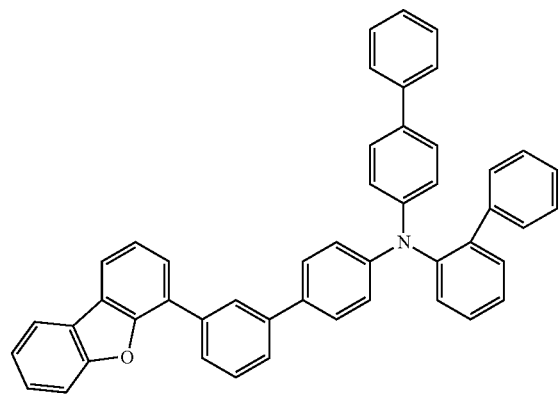
5
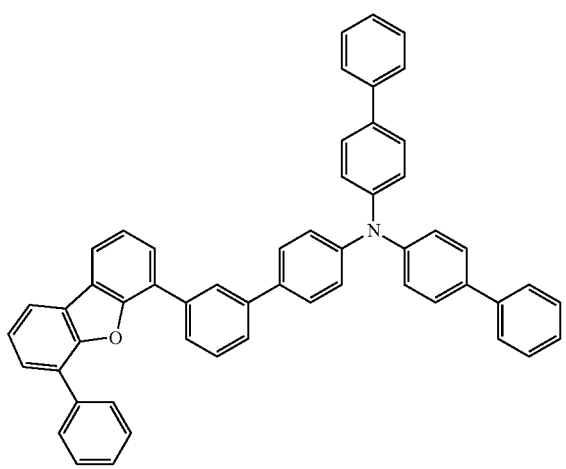
6
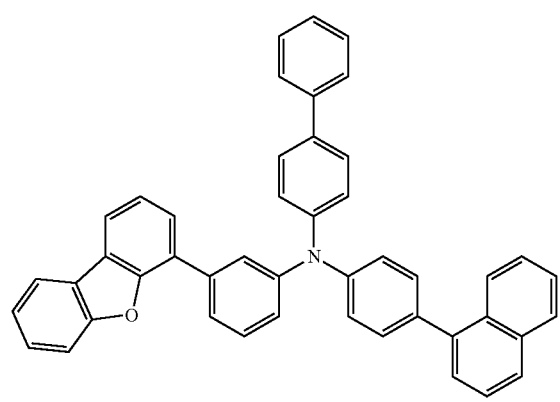
7
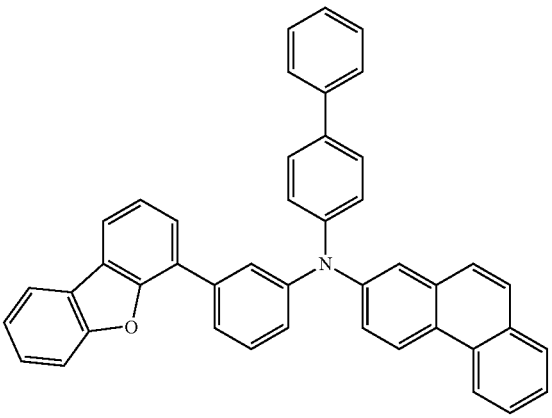
8
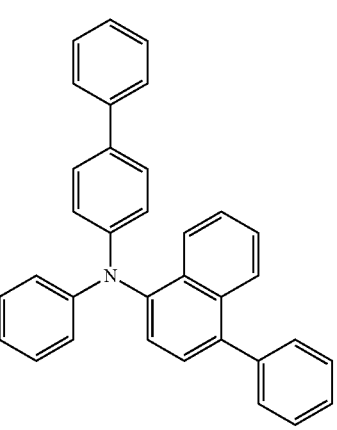
9
10

11
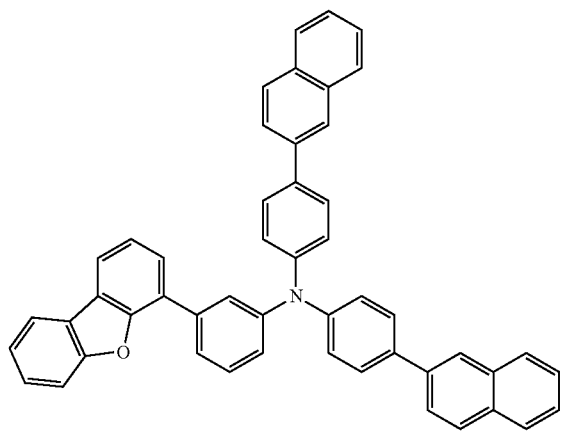
12
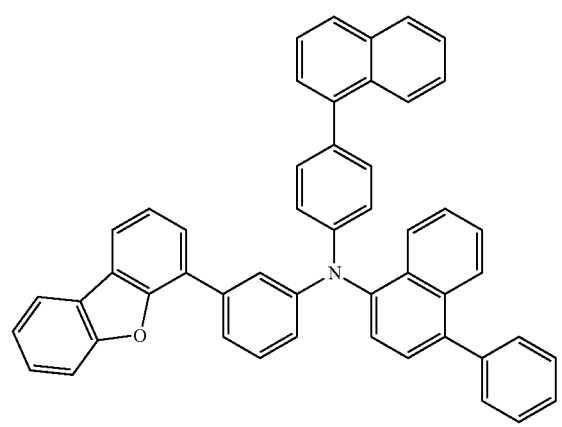
13
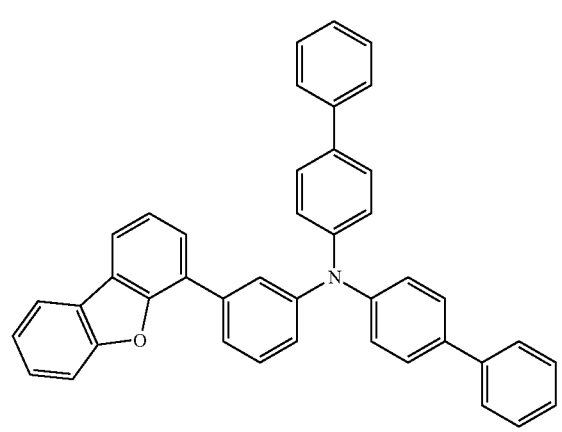
14
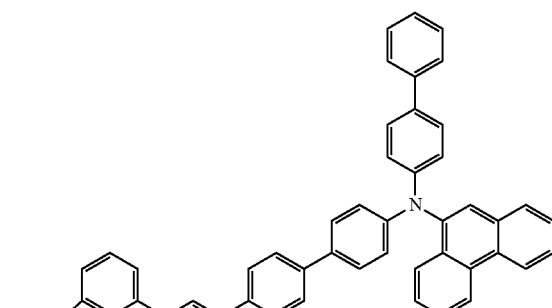
15
16
17
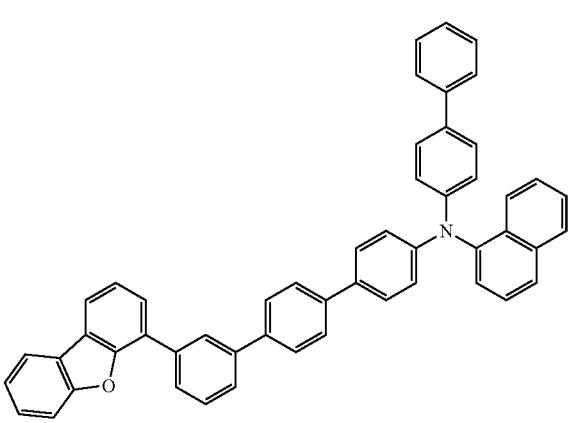

18
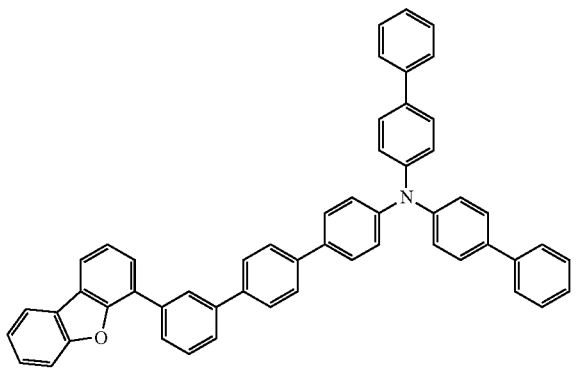
19
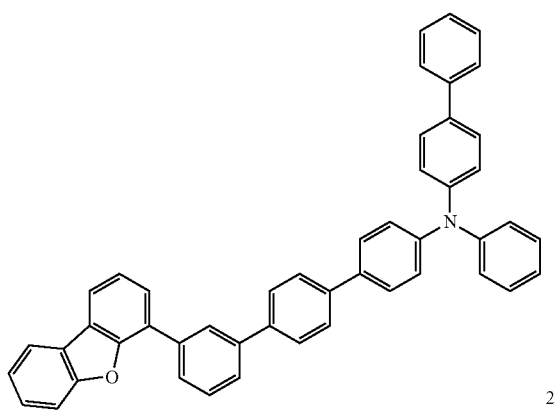
20
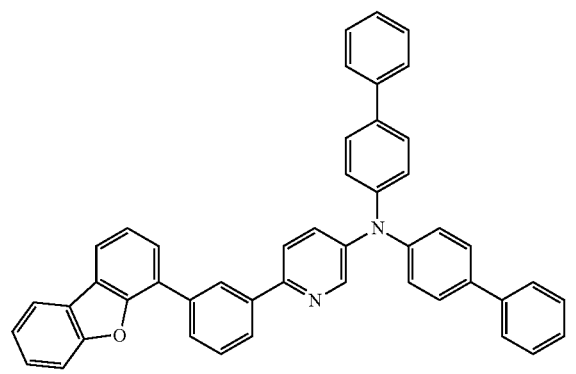
21
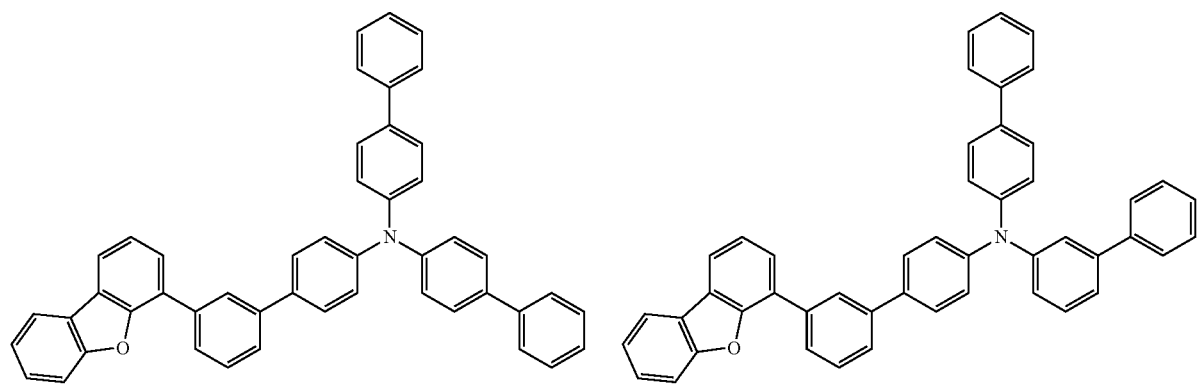
22
13. The organic EL device of claim 12, wherein the material for an organic EL device of Formula 1 is one selected from the group consisting of compounds 1 to 19:
1
2

3
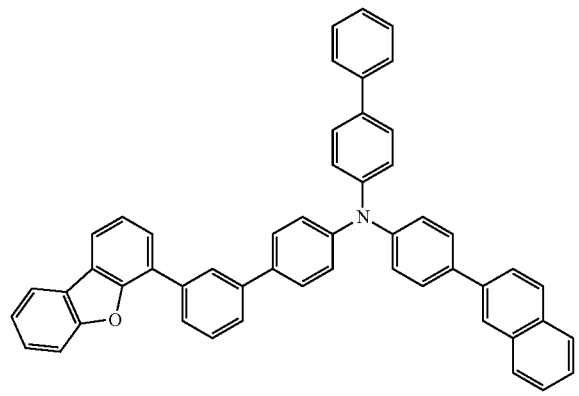
4
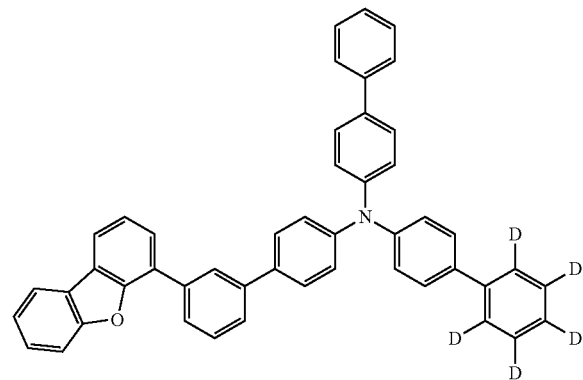
5
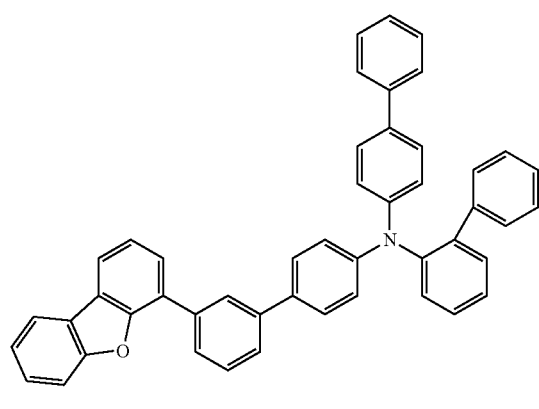
6
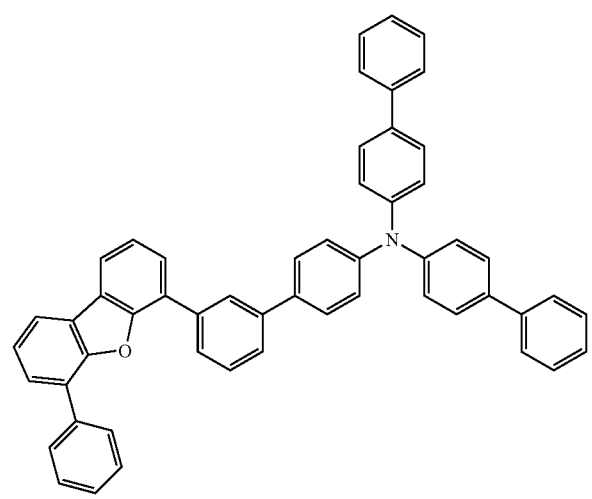
7
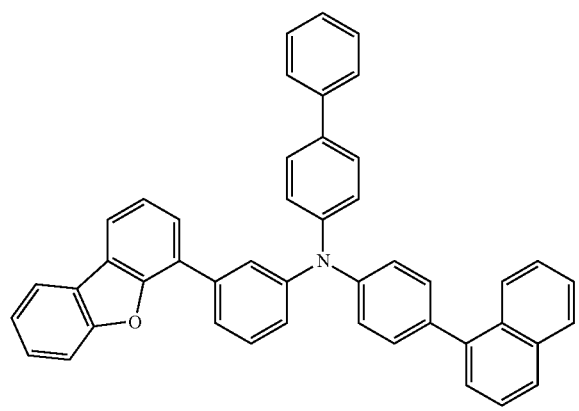
8
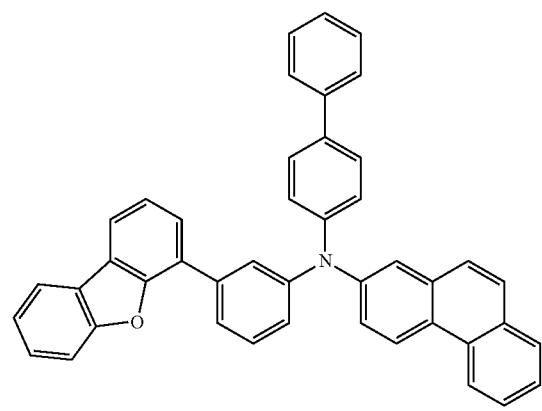

-continued
9
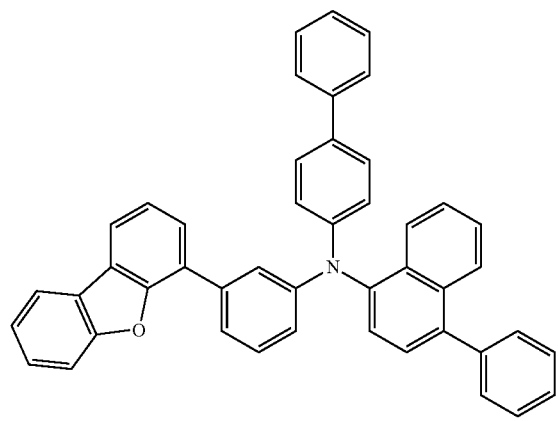
10
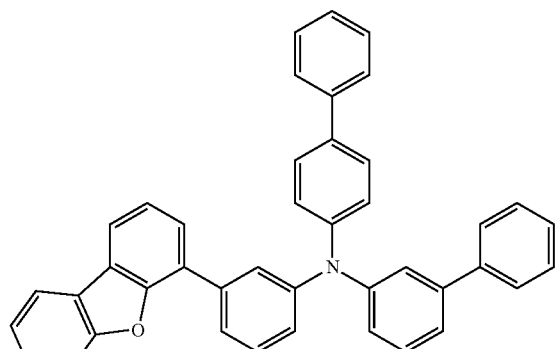
11
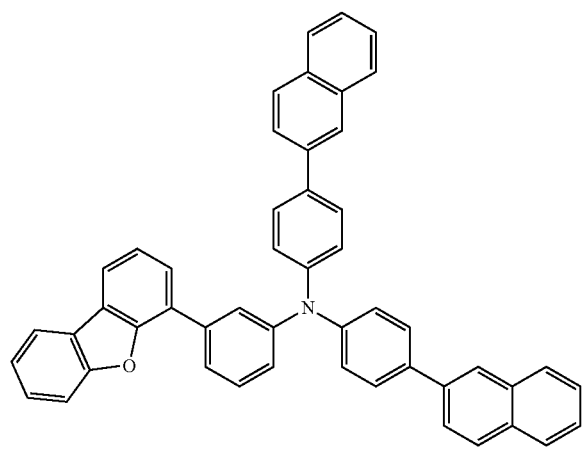
12
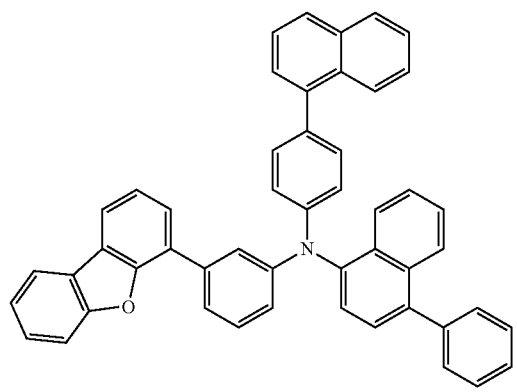
13
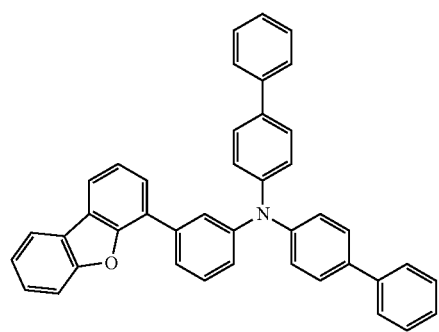
14
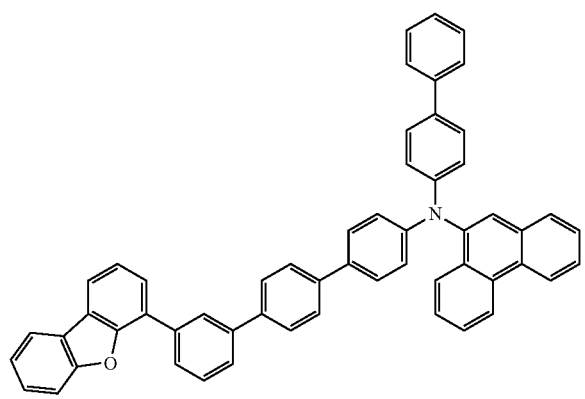

15
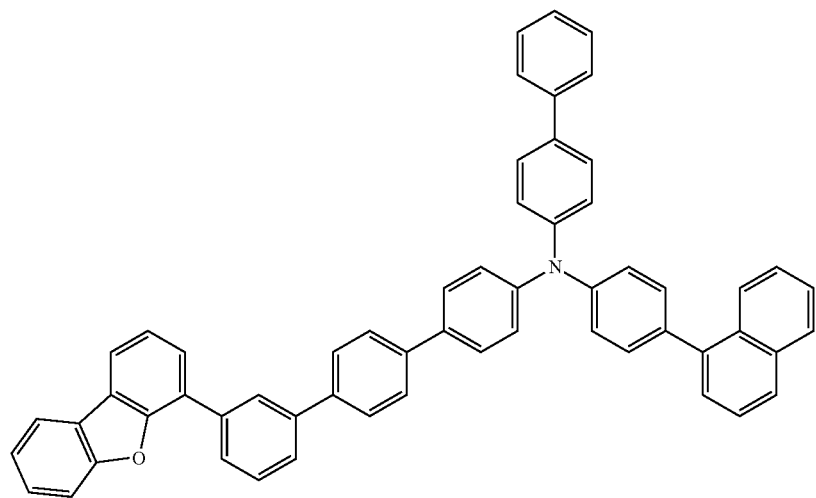
16
17
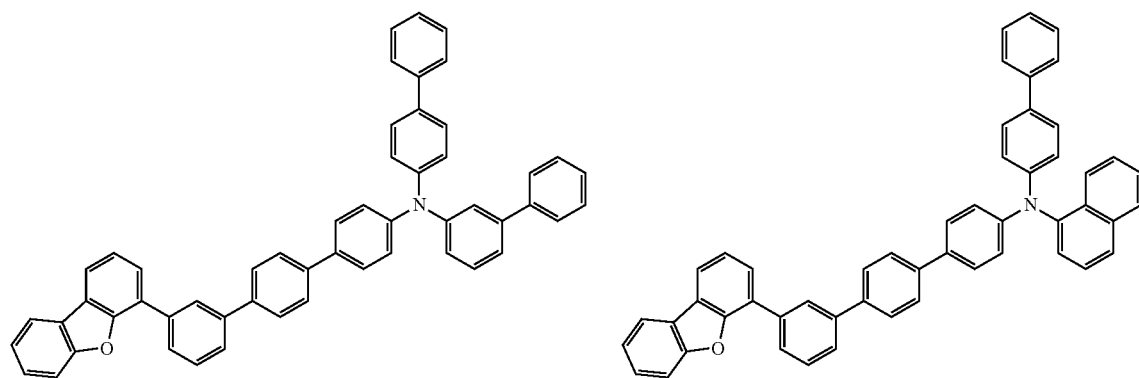
18
19
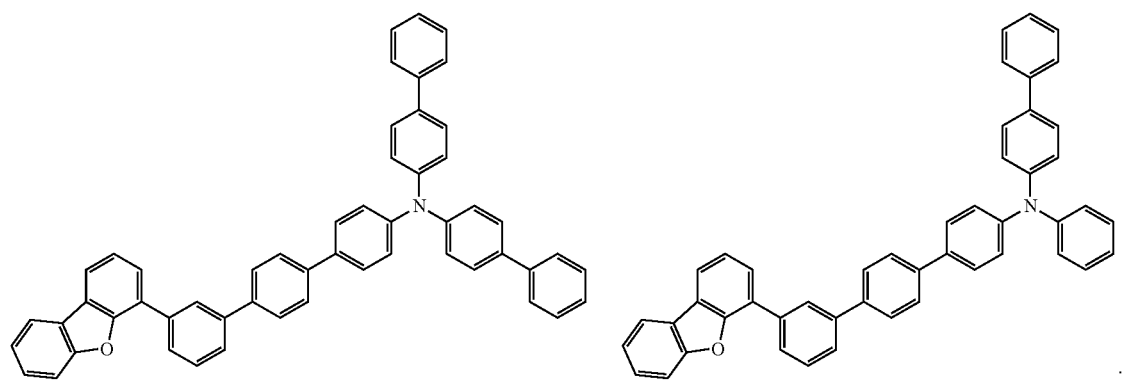

14. The organic EL device of claim 12, wherein the material represented by Formula 1 is one selected from the group consisting of compounds 20 to 22:
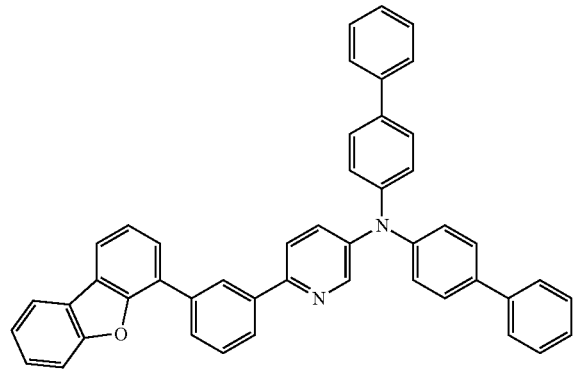
20
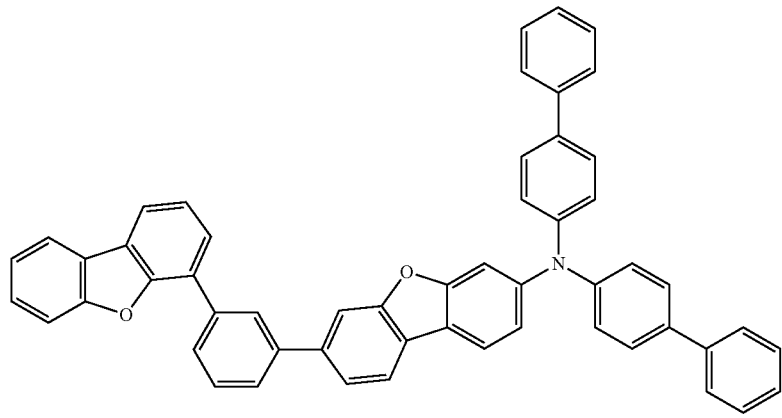
21
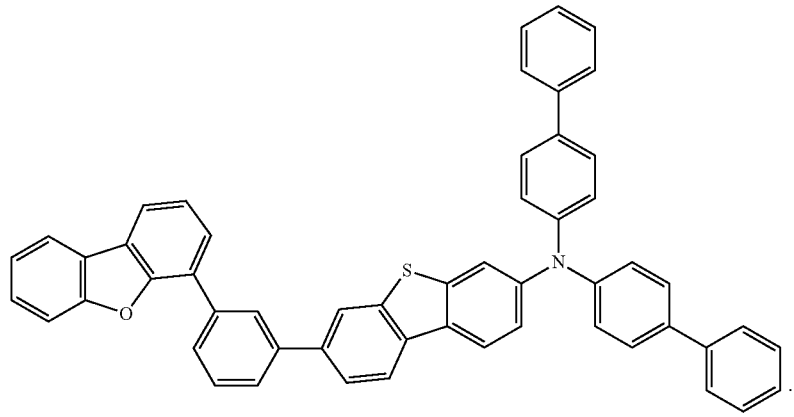
22